United States Patent [19]
Lapidus et al.

[11] Patent Number: 5,269,918
[45] Date of Patent: Dec. 14, 1993

[54] CLINICAL CARTRIDGE APPARATUS

[75] Inventors: Stanley N. Lapidus, Bedford, N.H.; Lewis T. Polk, Jr., Bedford; Arlen M. O'Lari, Chelmsford, both of Mass.

[73] Assignee: Cytyc Corporation, Malborough, Mass.

[21] Appl. No.: 948,304

[22] Filed: Sep. 21, 1992

Related U.S. Application Data

[63] Continuation-in-part of Ser. No. 937,247, Aug. 28, 1992, which is a continuation of Ser. No. 550,142, Jul. 9, 1990, Pat. No. 5,143,627.

[51] Int. Cl.$^5$ ............................................. B01D 35/00
[52] U.S. Cl. ................... 210/232; 210/252; 210/259; 210/295; 422/103; 422/104
[58] Field of Search ............... 210/142, 143, 232, 241, 210/252, 295, 259; 422/58, 62, 63, 99, 103, 101, 104

[56] References Cited

U.S. PATENT DOCUMENTS

| | | |
|---|---|---|
| 3,647,632 | 3/1972 | Johnson et al. |
| 3,900,290 | 8/1975 | Honstra ................... 422/73 |
| 4,166,768 | 9/1979 | Tolbert et al. ............. 435/286 |
| 4,391,710 | 7/1983 | Gordon .................... 210/361 |
| 4,395,493 | 7/1983 | Zahniser et al. ........... 435/289 |
| 4,435,507 | 3/1984 | Stenkvist ................. 435/262 |
| 4,468,410 | 8/1984 | Zeya ...................... 427/2 |
| 4,583,396 | 4/1986 | Hunt et al. ............... 73/61.73 |
| 4,647,376 | 3/1987 | Galaj ..................... 210/297 |
| 4,670,147 | 6/1987 | Schoendorfer ............. 210/541 |
| 4,755,300 | 7/1988 | Fishel et al. ............. 210/650 |
| 4,790,942 | 12/1988 | Shmidt et al. ............. 210/650 |
| 5,019,512 | 5/1991 | Varecka et al. ............ 435/240.25 |
| 5,143,627 | 9/1992 | Lapidus et al. ............ 210/232 |

FOREIGN PATENT DOCUMENTS

| | | |
|---|---|---|
| 1178183 | 11/1984 | Canada . |
| 0224962 | 6/1987 | European Pat. Off. . |
| 0244999 | 11/1987 | European Pat. Off. . |
| 0368621 | 5/1990 | European Pat. Off. . |
| 3338782 | 5/1985 | Fed. Rep. of Germany . |
| 63-202372 | 8/1988 | Japan . |
| WO89/09279 | 10/1989 | PCT Int'l Appl. . |

Primary Examiner—Robert A. Dawson
Assistant Examiner—Sun Uk Kim
Attorney, Agent, or Firm—Lahive & Cockfield

[57] ABSTRACT

A cartridge-like holder or carrier for automatic operation with a specimen processor has a frame for removable and replaceable alignment in operative engagement with the specimen processor and has multiple supports, each of which removably and replaceably supports an implement such as a container of a biological specimen having cellular particles suspended in a liquid, a filter device for use in collecting cellular particles from the liquid in the sample container, a viewing screen onto which the collected cellular particles can be transferred from the filter device and, further, an output container for receiving the viewing screen with the cellular particles thereon. A transfer mechanism on the apparatus is operable for the automatic transfer of the viewing screen from a support on the frame, where it received the cellular particles, to an output container at a further support on the frame. The cartridge apparatus brings to the specimen processor the sample and all disposable devices, i.e., sample contacting implements, and receives the final prepared specimen and all waste materials and disposables, thereby leaving the processor clean of contact with the sample and operative with successive samples, by way of separate cartridges, without inter-sample cleaning and without risk of inter-sample contamination.

17 Claims, 17 Drawing Sheets

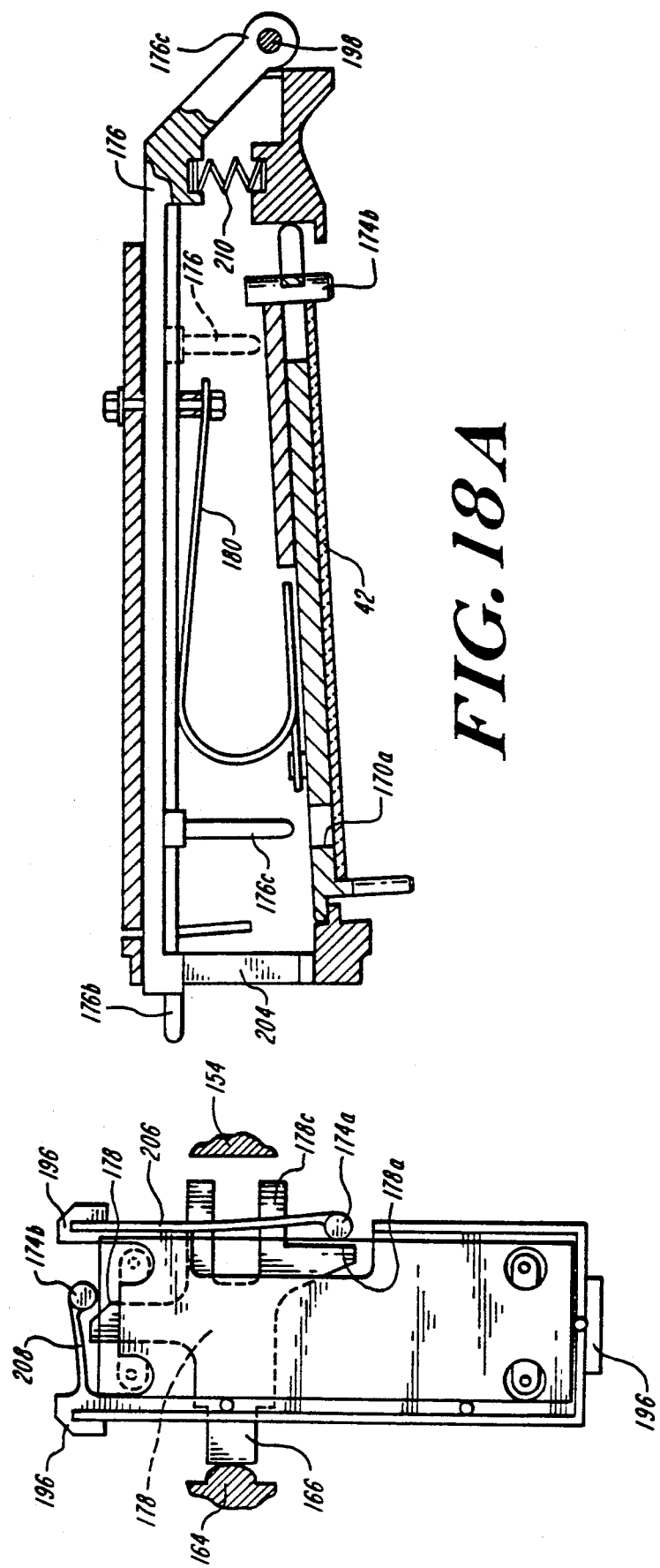

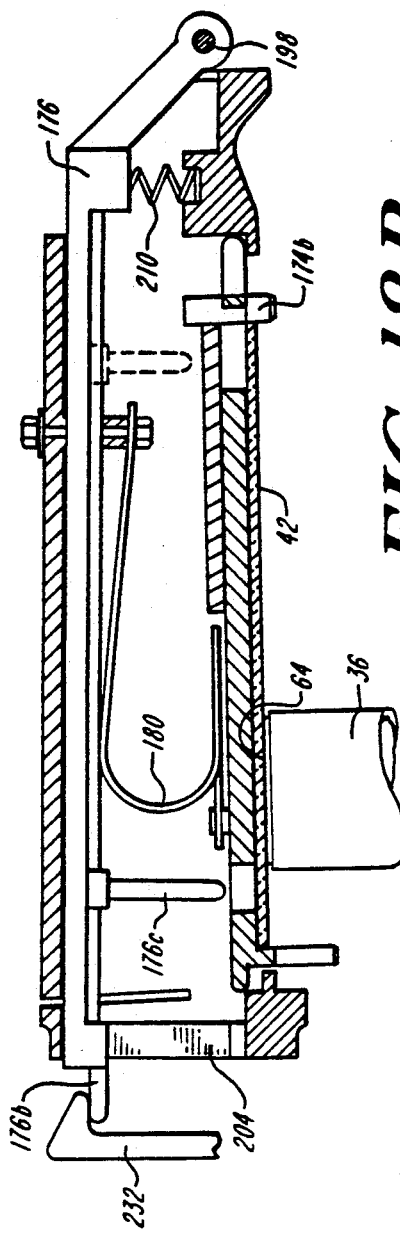
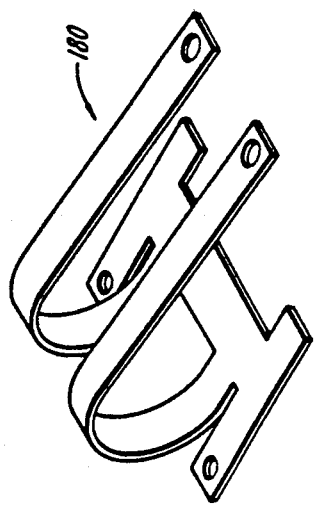
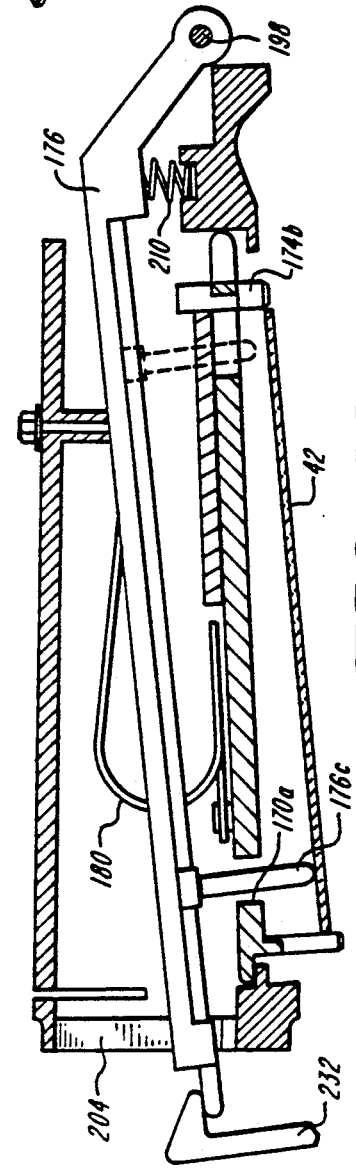
FIG. 18B
FIG. 18D
FIG. 18C

CLINICAL CARTRIDGE APPARATUS

CROSS REFERENCE

This application is related to the commonly assigned and concurrently filed application for patent Ser. No. 948,133 entitled "Specimen Processor Method And Apparatus", and is a continuation-in-part of the copending and commonly assigned U.S. patent application Ser. No. 937,247, filed on Aug. 28, 1992, entitled "Method And Apparatus For Preparing Cells For Examination", which is a continuation of U.S. patent application Ser. No. 550,142 now U.S. Pat. No. 5,143,627, issued Sep. 1, 1992.

BACKGROUND

This invention relates to a cartridge-like transport or holder for introducing sample material to a processing instrument and for receiving a biological specimen prepared from the sample material.

The cartridge apparatus of the invention is advantageously used, in at least one instance, in the clinical laboratory processing of a biological sample. More particularly, it is used in clinical laboratory processing in which cellular particles are collected from a liquid suspension of the sample and transferred to a microscope slide for examination, either electro-optically or by human viewing. The cellular particles are, as is advantageous, applied to the slide with essentially a monolayer and uniform distribution.

The term "cellular particles" is used herein to encompass cells, cell fragments and clusters or groups of cells and/or cell fragments. Clinical laboratory diagnostic testing with a monolayer distribution of cellular particles on a microscope slide, and apparatus and methods for performing such testing of the type with which the invention is advantageously practiced, are described in U.S. Pat. No. 5,143,627, in co-pending U.S. application for patent Ser. No. 843,571 and in the commonly assigned and concurrently filed application entitled "Automated Specimen Processor Method and Apparatus". The disclosures of these documents are incorporated herein by this reference.

The U.S. Pat. No. 5,143,627 describes an instrument for collecting a quantitatively measured number of biological cellular particles from suspension in a liquid sample and for transferring the counted collected particles, with an essentially monolayer and uniform distribution, to a viewing screen, typically a microscope slide. The instrument has disposable elements and containers that contact the sample material and accordingly that require replacement between the processing of successive samples, to avoid inter-sample contamination.

OBJECTS

It is an object of this invention to provide apparatus, for use in the preparation of a spatially distributed cellular specimen on a microscope slide or other viewing screen, with minimal concern for inter-sample contamination. Further general and specific objects of the invention will in part be obvious and will in part appear hereinafter.

SUMMARY OF THE INVENTION

Apparatus according to the invention enables a machine, termed a specimen processor, to process a biological sample to prepare a cytologic or other clinical specimen for examination, and isolates sources of inter-sample contamination from the specimen processor. The invention thus enables the specimen processor to process successive samples without cleaning and without risk of inter-sample contamination.

More particularly, the invention provides a cartridge-like holder or carrier apparatus for operation with a mechanized processor that collects cellular particles from a fluid sample and transfers the particles with a selected distribution to a microscope slide or like viewing screen. A cartridge according to the invention carries the sample material and all implements that come in contact with the sample. It is arranged so that the mechanized processor is not contaminated by the sample material.

A separate, fresh cartridge according to the invention is employed for each biological sample. Each cartridge brings to the mechanized processor the sample and all disposable devices, i.e., sample contacting implements. Further, the cartridge receives the final prepared specimen and all waste materials and disposables. The mechanized processor, as a result, remains clean of contact with the sample and can operate with successive samples, by way of separate cartridges, without inter-sample cleaning and without risk of inter-sample contamination.

A cartridge according to the invention has a frame that has a reference structure that removably and replaceably aligns and engages with a specimen processor. A preferred embodiment of the frame has a set of three triangularly disposed reference structures. A further preferred feature is that one reference structure is located along, and ensures alignment with respect to, a first axis. Two other reference structures, in this embodiment, are located along a second axis transverse to the first axis.

The cartridge frame has a first support for carrying a container of a biological sample and has at least one further support for carrying an implement that receives a specimen of the biological sample.

When the cartridge is engaged with the sample processor, the processor operates with the cartridge to transfer a specimen of the biological sample to the implement carried at the further support.

In a preferred embodiment, the cartridge has two further supports, and carries two implements. One implement is a filter device that the processor manipulates to separate constituents of the biological sample and to collect selected cellular particles from the sample. The particles are collected on a surface of a screen filter element of the filter device by drawing sample fluid, in which the cellular particles are suspended, through the screen filter element.

The cartridge preferably mounts the filter device at a known three-coordinate location and with selected rotational alignment about a further coordinate, namely, a rotation axis. Moreover, the cartridge in this embodiment mounts the filter device aligned directly above the location of a sample container on the cartridge. The rotation axis is preferably the first axis noted above with respect to which one reference structure is aligned. A further feature is that this one reference structure, the support for the filter device and the support for the sample container are selectively aligned and positioned with respect to the first axis.

The other implement that the cartridge mounts at a support is a microscope slide or like viewing screen.

The processor manipulates the filter device to transfer the collected cellular particles from the screen filter to the viewing screen, with essentially a printing operation.

At this stage of operation with a specimen processor, the cartridge of the invention carries the sample container and the viewing screen that now has a specimen of cellular particles on it. In addition, the cartridge, supports the filter device, which the specimen processor has returned to its support on the cartridge.

Further features of a cartridge according to the invention, are that it has an output support, for an output container, and has a transfer mechanism. In response to further operative engagement of the cartridge with a specimen processor, the transfer mechanism transfers the viewing screen, with a biological specimen on it, to the output container. In one practice, the output container contains a chemical fixative solution for fixing the specimen on the viewing screen.

Upon removal of the cartridge from the processor, the viewing screen on the cartridge carries a biological specimen and the screen is in the fixative solution ready for further processing. The cartridge also carries the container of the remaining biological sample, and it carries the filter device that was used to collect the biological cellular particles from the sample container and transfer them to the viewing screen. The specimen processor has no residue of the sample and has no waste material or contaminated parts or implements; it accordingly is ready immediately to repeat the foregoing cycle of operations with another cartridge carrying a fresh sample, a fresh filter device, a fresh viewing screen, and a fresh output container.

A cartridge according to the invention thus has supports for a sample container, for each specimen receiving implement, i.e., the filter device and the viewing screen, and for an output container. The cartridge supports are at known locations and in known alignment relative to the reference structures that engage with a specimen processor. Further, each support provides removable and replaceable support for the sample container, the filter implement, the viewing screen implement, and the output container, respectively. The removable and replaceable support for the sample container and for the output container allows a fresh container of each type to be installed on the cartridge prior to engagement with the specimen processor and to be removed after engagement with a specimen processor to prepare the cartridge for re-use. The removable and replaceable support for the filter device allows a fresh filter device to be loaded onto the cartridge, and enables the specimen processor to engage the filter device, remove it from its support on the cartridge, to manipulate it for the specimen preparation operations, and ultimately to return it to support by the cartridge; and ultimately for replacement with a fresh filter device, in preparing the cartridge for re-use. The removable and replaceable support for the viewing screen allows a fresh viewing screen to be loaded onto the cartridge, and to be disposed for receiving a specimen by transfer from the filter device. This support also allows the viewing screen to be released for transfer to the output container, in cooperation with the specimen processor. In addition, the cartridge support for the viewing screen enables the viewing screen to undergo selected movement, upon engagement by a filter device during the transfer of collected cellular particles from the filter device to the viewing screen.

As noted above, two supports on a preferred cartridge, i.e., the filter implement support and the sample container, are aligned along a first axis. That axis is normally vertical. Two other supports, i.e., the viewing implement support and the output support, are preferably aligned along a plane passing through the first axis. A further feature of the invention is that the several supports provided by a cartridge according to the invention are disposed successively along a curved, planar path. In the illustrated preferred embodiment, the order of the succession is, starting with the filter implement support, the viewing implement support, the output support, and the sample support. It further is preferred that the supports be disposed at progressively different elevations, with the filter implement support uppermost, followed in order by the viewing implement support, the output support, and the sample support.

Further features of the invention are that the viewing implement support has a load position, for receiving a microscope slide or other viewing screen, and a specimen receiving position, for receiving a biological specimen onto the viewing implement. The support clamps the loaded viewing implement in the transition from the load position to the specimen receiving position. Features of a preferred transfer mechanism according to the invention are that it removes the viewing implement from the implement support, when in the specimen receiving and clamped positions, and transfers the implement to an output container, at the cartridge output support, by guiding the gravitational pull of the implement.

The invention accordingly comprises the features of construction, combinations of elements and arrangements of parts exemplified in the constructions hereinafter set forth, all as exemplified in the following detailed disclosure, and the scope of the invention as indicated in the claims.

BRIEF DESCRIPTION OF THE DRAWING

For a fuller understanding of the nature and objects of the invention, reference is to be made to the following detailed description and the accompanying drawings, in which:

FIG. 17 is a fragmentary simplified view, opposite to the view shown in FIG. 15, showing the slide holder and camming plate of the cartridge cradle assembly according to the invention;

FIGS. 18A, 18B and 18C are simplified fragmentary elevation views showing features of the cradle assembly according to the invention with different positions of the ejector arm and of the slide holder; and FIG. 18D is a detail of FIG. 18C showing a leaf spring for the cradle assembly according to the invention.

DESCRIPTION OF ILLUSTRATED EMBODIMENT

Figure 1:
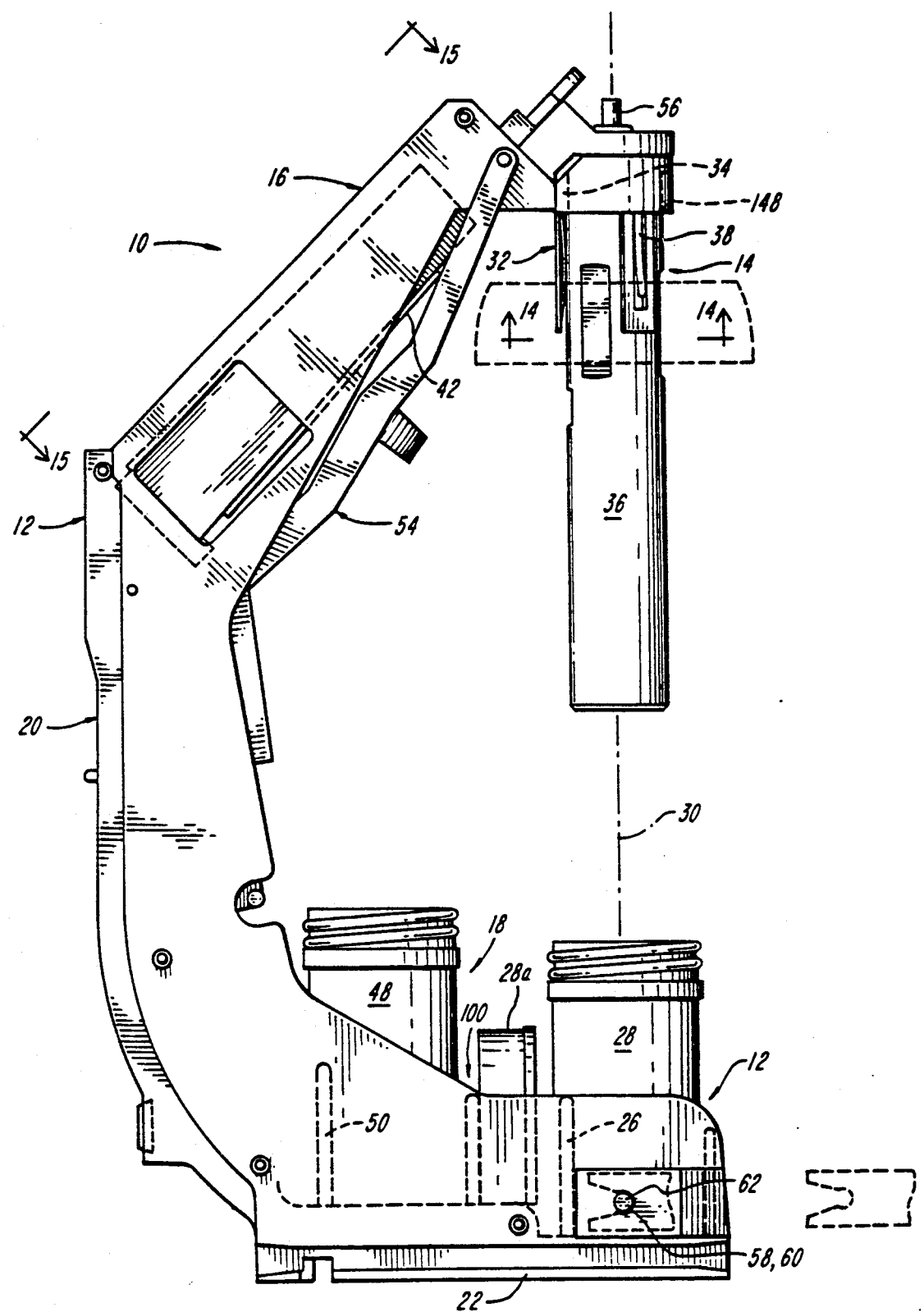
FIG. 1 is a side elevation view of a cartridge according to the invention carrying a sample container, an output container, a microscope slide, and a filter device.
Figure 2:
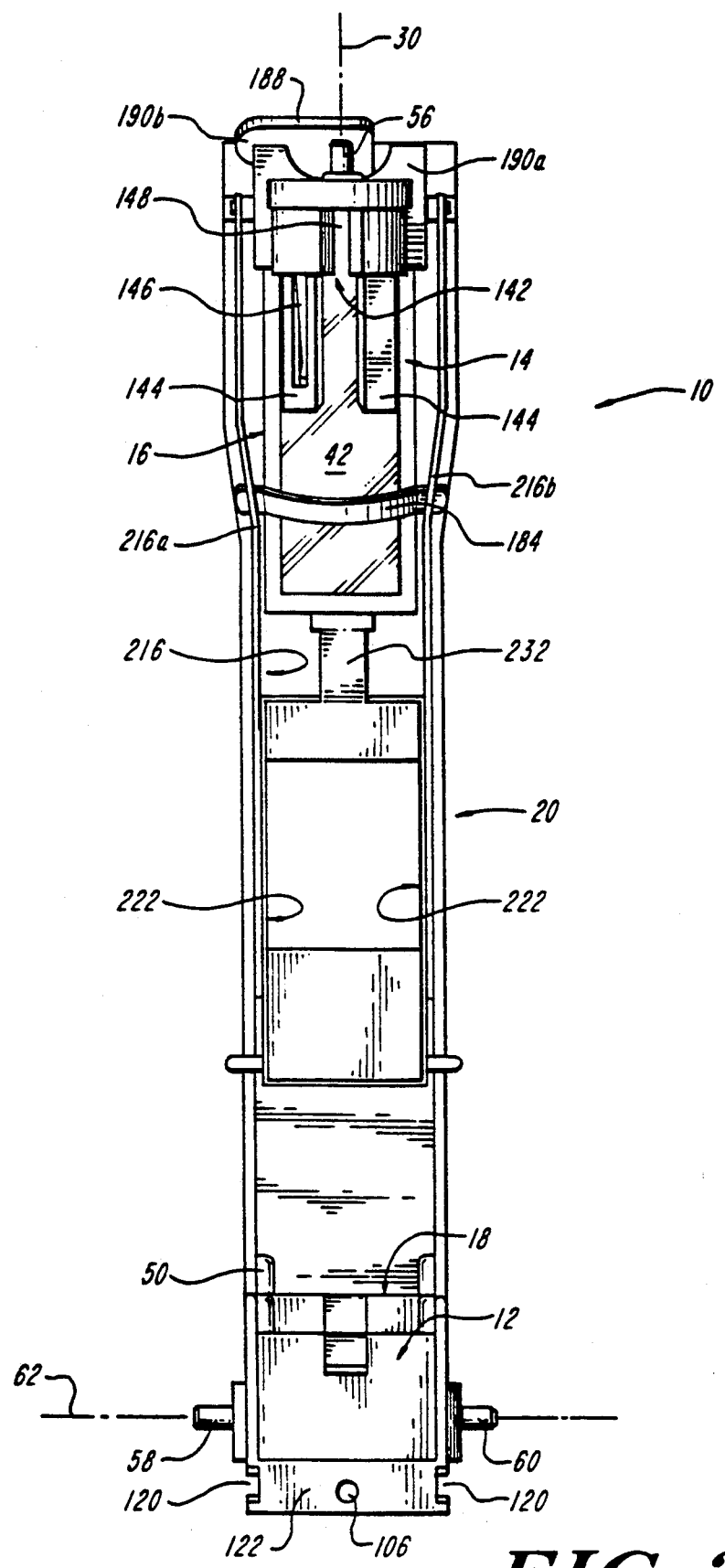
FIG. 2 is a front elevation view of the cartridge of FIG. 1.

FIGS. 1 and 2 show a cartridge 10 according to the invention for operation with a specimen processor, as discussed below with references to FIGS. 4-10. The cartridge 10 has an upright frame 20 with a base 22, and has four supports 12, 14, 16, and 18, each of which removably and replaceably receives and holds a clinical implement.

A first of the four supports is a sample support 12, lowermost on the illustrated cartridge 10, and formed with upright sample guides 26. The sample guides 26 and base 22 form the sample support 12 as essentially a socket-like receptacle that telescopically receives a sample container 28 oriented upright and centered on a normally vertical axis 30.

A second support on the cartridge 10 is a first implement support 14 located uppermost on the cartridge, adjacent the top of the frame 20. The first implement support 14 includes a downwardly facing tubular socket-like receptacle 32 centered on the axis 30. The support 14 includes a rotational guide, illustratively formed with an axial slot 34 recessing the wall of the receptacle 32, for imparting a selected rotational orientation, relative to the vertical axis 30, of a filter device 36 seated therein. The illustrated implement support 14 also has a leaf spring 38 arranged for resiliently engaging a filter device 36 seated in the support for removably and replaceably holding the filter device in the support.

A third support on the cartridge is a second implement support 16 for holding a microscope slide 42. The illustrated support 16 has a breach-like mechanism into which a slide 42 is loaded and then clamped. The support positions the clamped slide to receive a distribution of cellular particles collected from a sample in the sample container 28.

The illustrated fourth support is an output support 18 that can be structured similar to the sample container support 12 to receive an output container 48 at a selected lower location on the cartridge 10. The illustrated output support 18 accordingly employs upright container guides 50 that, together with the base 22, provide a socket-like receptacle for receiving and locating an upright output container 48.

A further feature of the illustrated cartridge 10 is a transfer mechanism 54 on the frame 20 that, as described further below and shown in FIG. 11, removes a microscope slide 42 from the support 16 and transfers it to an output container 48 at the output support 18. The illustrated transfer mechanism 54 guides the gravitational descent of a microscope slide 42 that has been released from the second support 16, for transferring the slide into an output container 48 seated in the output support 18

The illustrated cartridge 10 has three triangularly located reference structures, illustrated as cylindrical reference pins 56, 58, and 60, for removeable and replaceable engagement with mating reference structures of a specimen processor. Two reference pins 58 and 60 project in opposite directions from the frame 20 along a normally horizontal axis 62 transverse to the vertical axis 30. The third reference pin 56 projects from the top of the cartridge frame 20 and is axially centered and aligned with the vertical axis 30.

The supports 12 and 14 and the reference pin 56 of the illustrated cartridge 10 are aligned and centered on the normally vertical axis 30. Accordingly, the sample container 28 seated in the support 12 and the filter device 36 seated in the support 14 are likewise aligned and centered on the axis 30. Further, the illustrated four supports are aligned along and centered on a plane through the axis 30 and parallel to the plane of FIG. 1.

Figure 3:
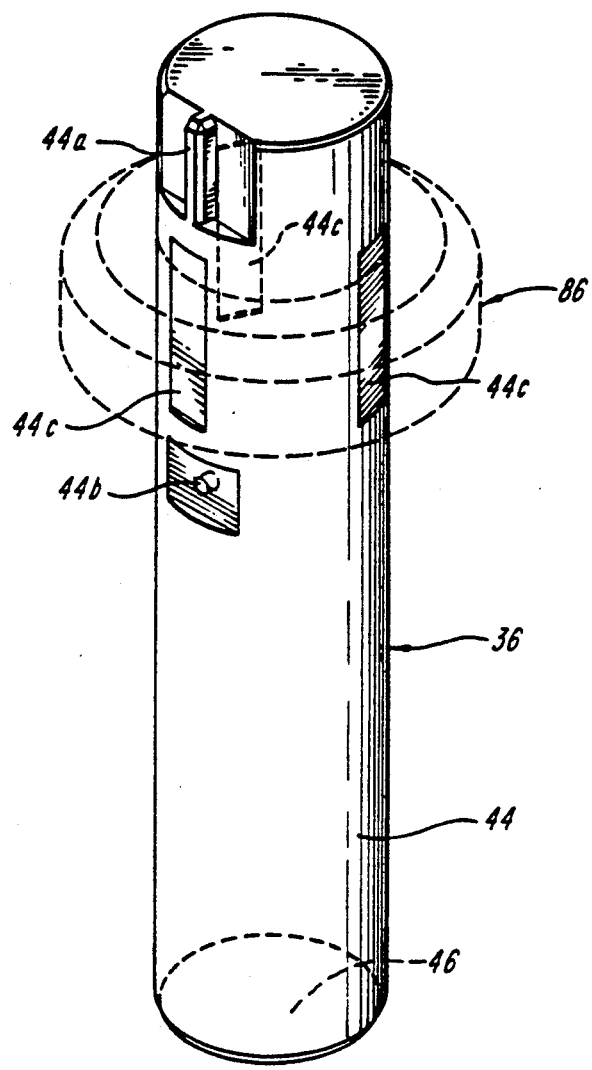
FIG. 3 is a perspective view of a filter device for use with the cartridge of FIGS. 1 and 2.

The illustrated filter device 36, shown in FIG. 3, has a hollow cylindrical body 44 closed at a normally upper axial end and having a screen filter 46 spanning across a normally lower axial end. The screen filter has pores of selected size to block cells and cellular particles of interest and to pass smaller particles. An orienting tab 44a projects radially from a flattened surface portion of the body, adjacent the closed end. The tab 44a is preferably within, and hence does not project beyond, the cylindrical outer surface of the body 44. A passage 44b extends radially through the wall of the body 44 at a location axially aligned with the tab 44a and well space from both axial ends to be in the middle portion of the body. The cylindrical outer surface of the body is flattened at the passage 44b, so that the passage extends from the center of the flattened recess in the body outer wall.

A further structure feature of the illustrated filter device 36 is a clamping region located axially between the aligning tab 44a and the passage 44b, and having a non-circular cross-section. The illustrated non-circular clamping region is formed by three flat clamping surfaces 44c uniformly spaced about the circumference of the cylindrical body 44. This set of clamping surfaces has a selected or known circumferential location and axial location on the device 36, relative to the tab 44a and the passage 44b. Co-pending and commonly-assigned U.S. Application for patent Ser. No. 07/843,571 discloses the structure and manufacture of filter devices similar to the filter device 36, and such similar filter devices are marketed by Cytyc Corporation of Marlborough, Mass., U.S.A.

Figure 4:
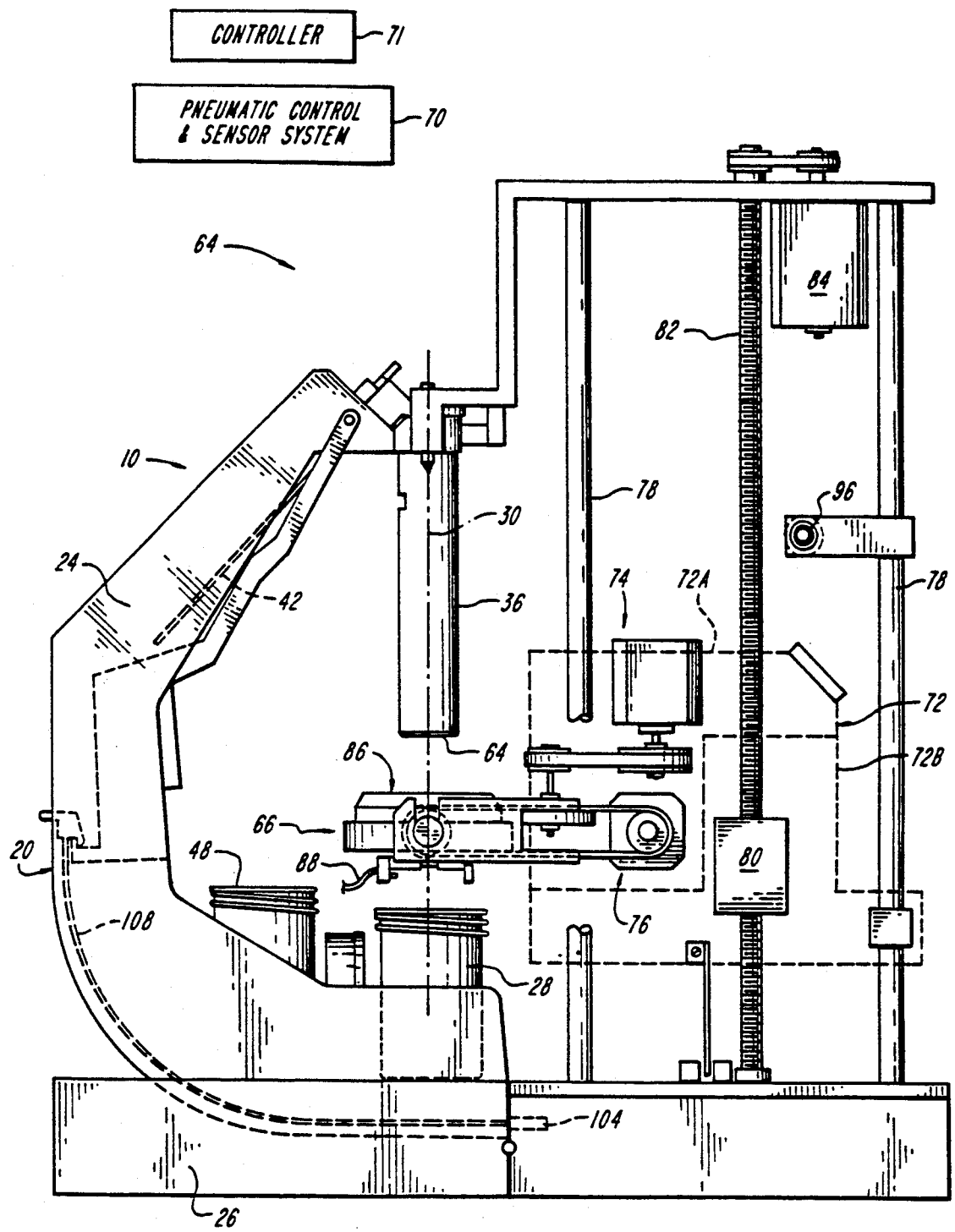
FIGS. 4 through 10 are side elevation views, partly simplified and partly diagramatic, of the cartridge of FIGS. 1 and 2 operatively engaged with a specimen processor and showing different stages of the processor operation with the cartridge according to the invention.

FIG. 4 shows the cartridge 10 of FIGS. 1 and 2 engaged with a specimen processor 64 of the type disclosed in the concurrently-filed and commonly assigned application identified above. The illustrated processor has a manipulator 66 coupled with a multi-axial drive system and coupled with a pneumatic control system 70. During operation of the specimen processor 64 with a cartridge 10, the manipulator 66 is aligned initially with the vertical axis 30 of the cartridge 10 as appears in FIG. 4 and disposed vertically above the sample container 28 and below the filter device 36 that the cartridge carries.

The illustrated processor 64 has an extendable two-part carriage 72 that mounts the manipulator 66 on a carriage platform 72a. The carriage platform 72a carries a rotational drive mechanism 74 coupled with the manipulator and carries a tilt drive mechanism 76 also coupled with the manipulator 66. A second carriage platform 72b carries the platform 72a and is slideably mounted on two parallel elevator slide rods 78. The second platform is coupled by way of a nut block 80 with a lead screw 82 driven by an elevator motor 84.

The specimen processor 64 operates with a controller 71, typically employing a micro processor, and with the pneumatic control and sensing system 70. EPO Publication No. 0448837A3 describes one preferred construction for the pneumatic system 70.

The cartridge 10 operates with the illustrated specimen processor 64 through a sequence of stages for collecting a biological specimen from the sample in the cartridge-carried container 28 and for transferring it to a microscope slide 42 carried on the support 16 of the cartridge.

Figure 5:
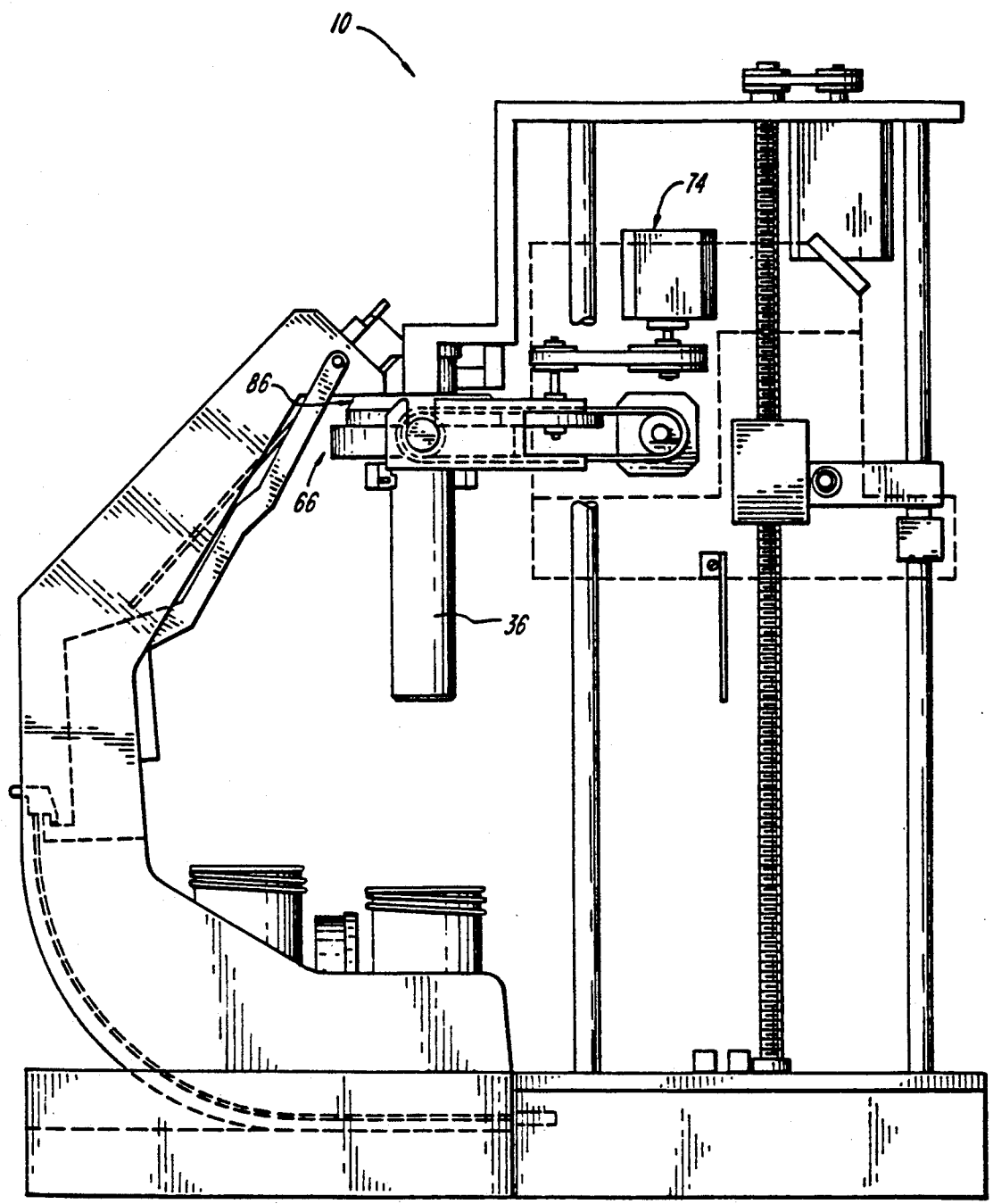

In a first operating stage, subsequent to the initial engagement stage in which the cartridge 10 is operatively engaged with the processor 64 as shown in FIG. 4, the elevator motor 84 rotates the lead screw 82 to raise the carriage 72 to an uppermost position shown in FIG. 5. This upward movement raises the manipulator 66 to slide upward relative to the filter device 36 mounted on the cartridge 10. The illustrated manipulator 66 has a circular jaw mechanism 86 centered on the axis 30 in the initial condition of FIG. 4 and that is initially in an unclamping condition where it telescopically fits over the body 44 of the filter device 36. The upward elevational movement of the carriage thus positions the manipulator 66 in the clamp position shown in FIG. 5, where the jaw mechanism 86 essentially encircles the filter device at the clamping surfaces 44c. The jaw mechanism has two jaw elements that can be locked to rotate together and that can be unlocked to rotate relative ton one another. This relative rotation moves radial clamping jaws into and out of clamping engagement with the body of the filter device 36.

With the processor 64 in the clamp position of FIG. 5, the rotational drive mechanism 74 operates the circular jaw mechanism 86 of the manipulator 66 to clamp the jaw mechanism onto the tubular body 44 of the filter device 36. The illustrated drive mechanism 74 performs this clamping operation by rotating one of two jaw elements of the jaw mechanism 86 about the vertical axis 30 relative to the other jaw element to affect a radially inward clamping action onto the three clamping surfaces 44c on the body of the filter device 36.

After clamping the manipulator 66 onto the filter device 36, the processor 64 rotates the lead screw 82 to lower the carriage 72 and thereby lower the manipulator 66. This downward movement of the manipulator 66 lowers the filter device 36, which is clamped to the manipulator, thereby removing the filter device 36 from the implement support 14 of the cartridge 10 and eventually immersing the lower end of the filter device into the biological sample contained in the sample container 28, as FIG. 6 shows.

Figure 6:
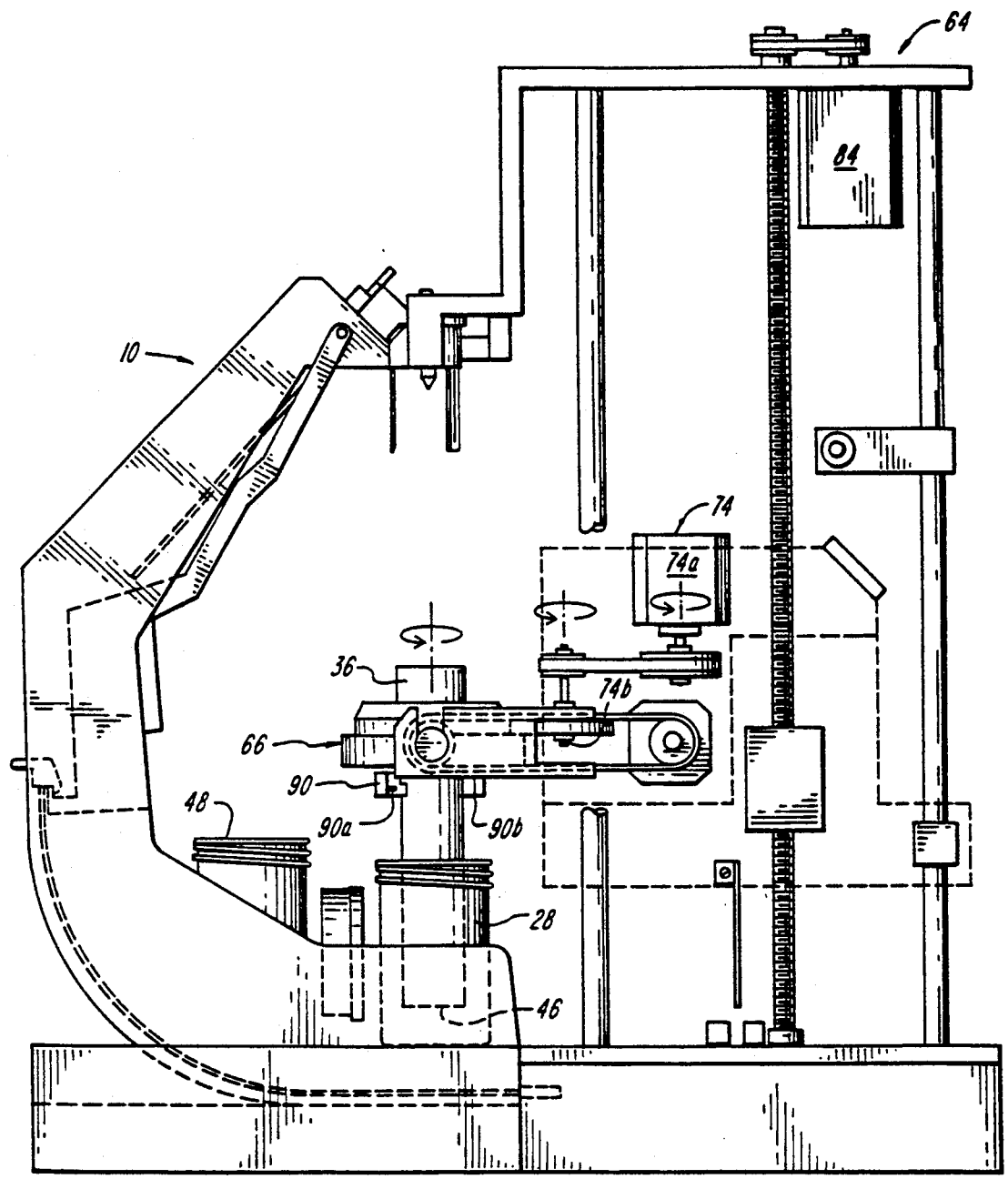

One operation of the specimen processor 64 when in the disperse position of FIG. 6 is to spin the filter device 36 about the vertical axis 30 to subject the biological sample in the container 28 to shear forces that disaggregate particles in the liquid sample solution. The illustrated processor 64, to this end, actuates the rotational drive mechanism 74 to spin the clamped filter device 36. In particular, the illustrated rotational drive mechanism 74 operates a motor 74a coupled by a belt and pulley with a shaft that carries a drive wheel 74b, the rim of which is engaged to rotate the jaw mechanism 86. FIG. 6 designates with the three arrows the rotation of the motor 74a, the rotation of the drive wheel 74b and the resultant rotation of the manipulator jaw mechanism 86 and the filter cylinder 36 clamped therein.

After this particle dispersing action, the processor controller 71 stops the drive mechanism 74 and actuates the pneumatic control system 70 for collecting a specimen of cellular particles from the sample in the container 28 onto the screen filter 46 of the filter device 36. The above-noted EPO Patent Publication No. 0448837A3 and U.S. Pat. No. 5,143,627 describe a preferred specimen collecting operation. For this operation, the pneumatic control system 70 applies a selected negative pressure, preferably a series of negative pressure pulses separated by pressure-sensing intervals, to the interior of the filter device 36 by way of a pneumatic hose 88 connected between the pneumatic system 70 and a pneumatic coupling clamp 90 on the manipulator 66.

Figure 7:
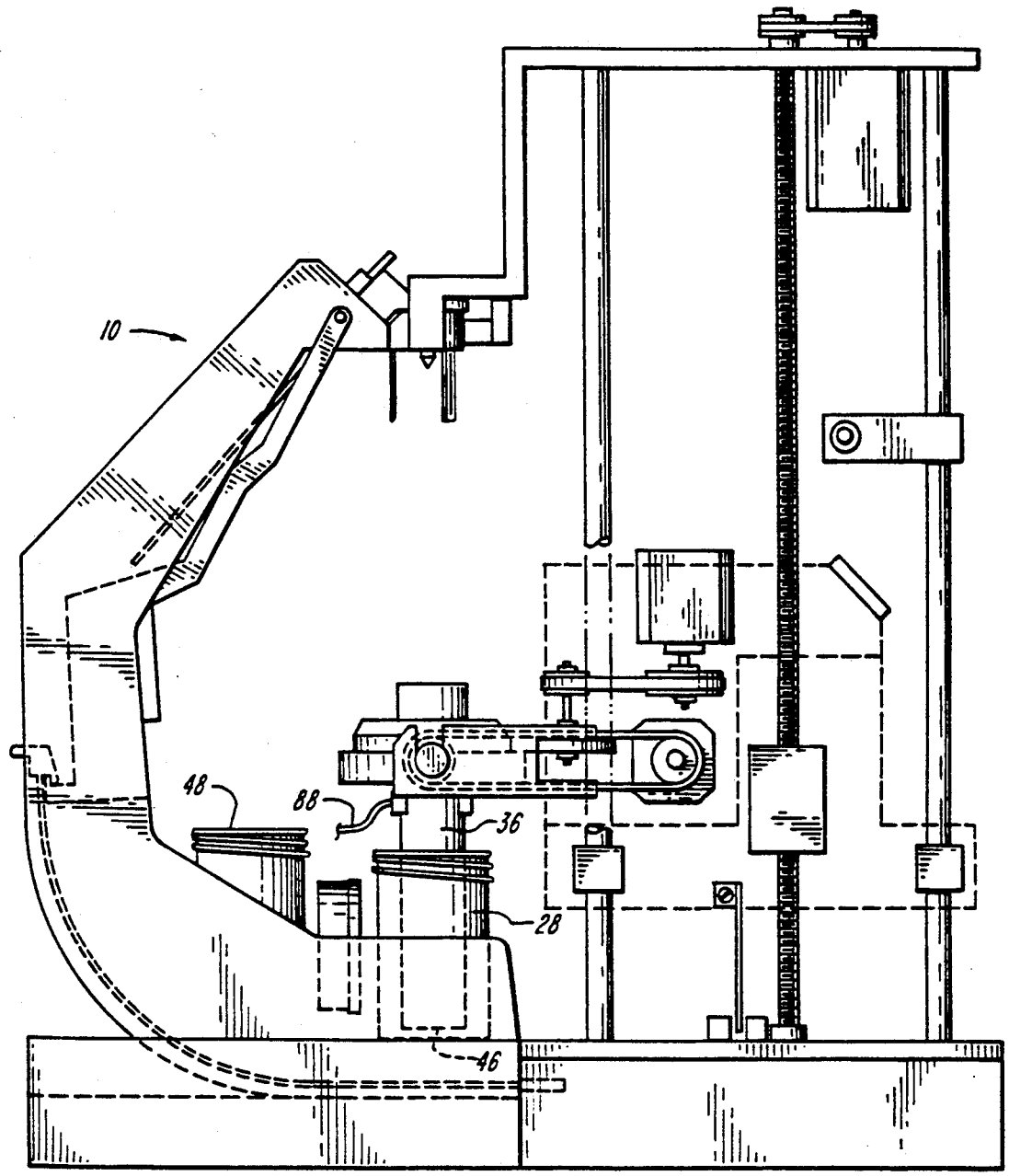

The illustrated pneumatic coupling clamp is a solenoid-actuated caliper, having caliper arms 90a and 90b disposed on opposite sides of the clamped filter device. The clamp 90 is open, with the clamp arms spaced away from the filter cylinder 36, when the processor 64 is in the position of FIGS. 4, 5 and 6. FIG. 7 shows the clamp in the closed condition, where the arms 90a and 90b are clamped against the body 44 of the filter device. The clamp arm 90a carries a pneumatic coupling, connected to an end of the hose 88, which connects to the filter device passage 44b (FIG. 3) when the clamp 90 is closed. In one preferred embodiment, the hose 88 has two separate passages and the clamp arm 90a forms a wye-like fitting that connects both hose passages in parallel to the filter device passage 44b. The pneumatic system 70 couples one passage of hose 88 to a pressure source and connects the other hose passage to a pressure sensor, for sensing pressure inside the chamber of the filter device 36.

Accordingly, when the clamp 90 is closed, FIG. 7, the pneumatic system 70 can apply a selected positive pressure signal, and conversely a selected negative pressure signal, to the interior chamber of the filter device. The pneumatic system applies a negative pressure signal to the filter device 36 to draw sample liquid into the device from the sample container 28, and thereby deposit cellular particles of the sample onto the filter screen of the filter device 36. After a selected quantity of cellular particles are collected on the screen filter of the filter device 36, as determined by sensing pressure in the interior chamber of the filter device with the pneumatic system 70 operating in conjunction with the controller 71, the pneumatic signal terminates.

The specimen processor 64 proceeds from the collection position of FIG. 7 to a transfer position with several steps. A first step is to raise the filter device 36 clamped in the manipulator 66, with the collected specimen of cellular particles on the screen filter 46, by operating the elevator motor 84 to raise the filter device sufficiently to withdraw it from the sample container 28.

Figure 8:
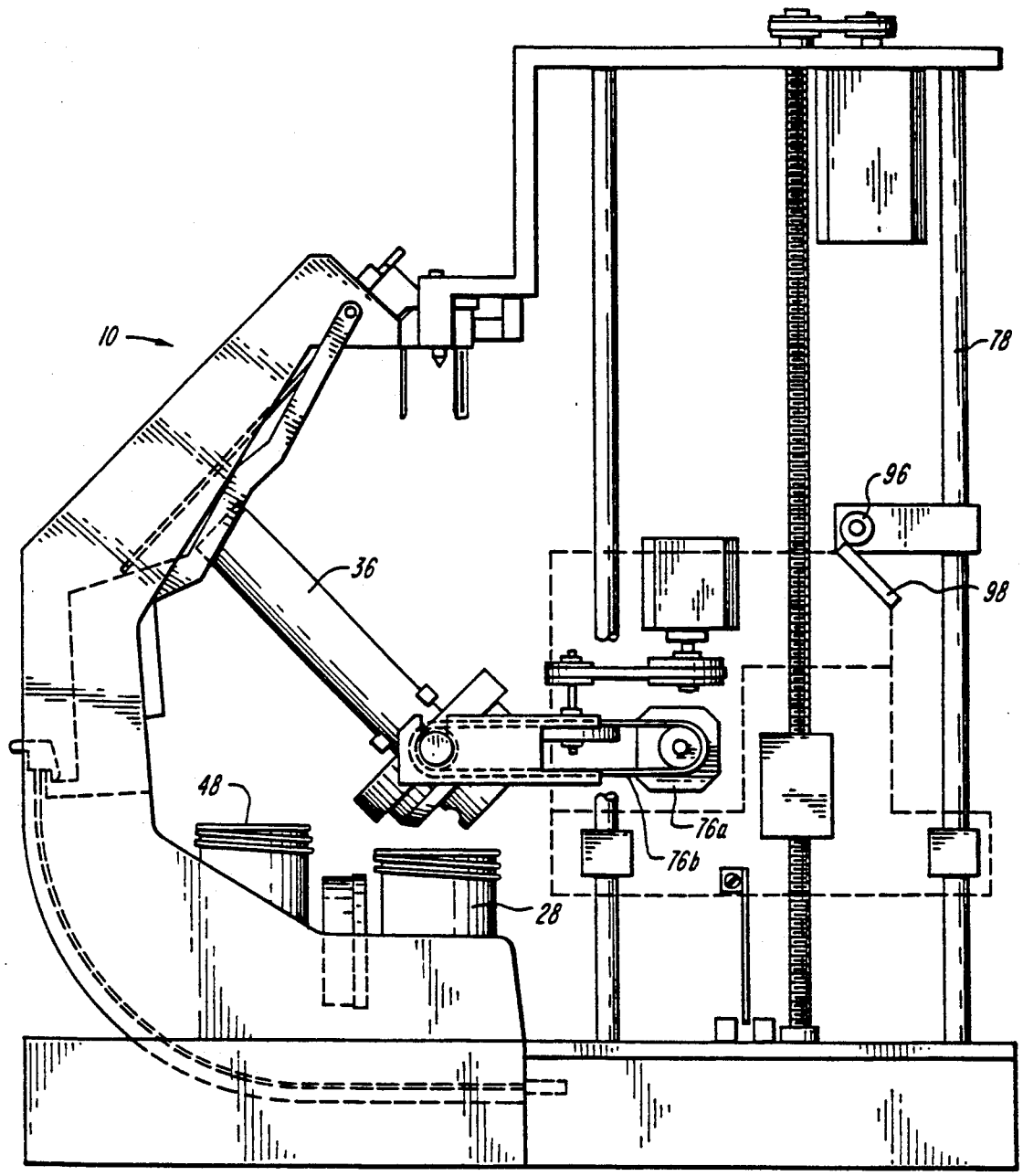

The specimen processor 64 executes a second step of this transition by actuating the tilt drive mechanism 76 to revolve the manipulator jaw mechanism 86, together with the filter device 36 clamped therein clockwise to the position shown in FIG. 8. This tilting movement is about a normally horizontal axis parallel to the horizontal axis 62 along which the cartridge reference pins 58 and 60 are aligned. A motor 76a of the tilt mechanism is coupled by a belt 76b with the jaw mechanism 76, for effecting the tilt movement.

Figure 9:
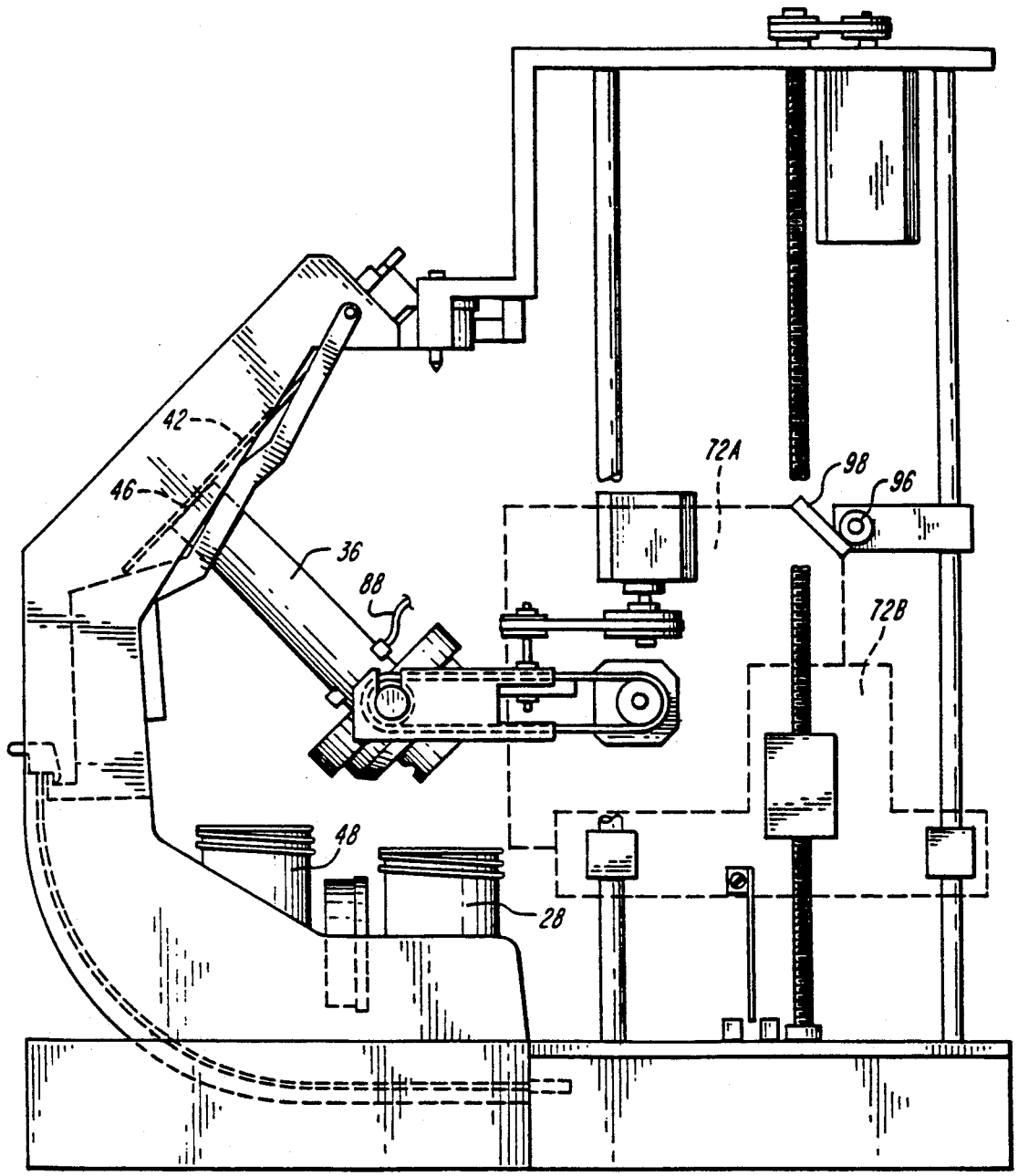

A subsequent operation of the specimen processor 64 with the illustrated cartridge 10 moves the clamped filter device 36 horizontally to the left, from the position of FIG. 8 to the extended position shown in FIG. 9. This movement abuts the screen filter 46 of the filter device against the microscope slide 42 that the cartridge carries at the support 16. This abutment of the screen filter with the microscope slide transfers cellular particles collected on the screen filter to the microscope slide. The transferred cellular particles have essentially the same spatial distribution on the microscope slide as they had on the screen filter, as is desired. A preferred concurrent operation is for the controller 71 to actuate the pneumatic system 70 to apply a small positive pneumatic pressure to the interior of the filter device 36, by way of the pneumatic clamp 90, for enhancing the lift-off of cellular particles from the screen filter and thereby enhancing the transfer of all collected cellular particles from the screen filter of the filter device to the microscope slide 42.

The illustrated specimen processor 64 affects the lateral movement of the clamped filter device 36 to the shifted or extended position shown in FIG. 9 by moving the platform 72a of the carriage 72 laterally relative to the other carriage platform 72b. The second carriage platform 72b mounts the first carriage platform 72a on two parallel and horizontally-extending slide rods 92, and a spring 94 is tensioned between the two platforms to maintain them normally in the retracted and aligned condition of FIGS. 4 through 7. Further, the processor 64 has a camming roller 96 mounted on one slide rod 78 and moveable, horizontally with a solenoid (not shown) to engage selectively with an inclined ramp 98, shown in FIG. 8 on the upper right side of the platform 72a, during upward movement of the carriage 72 from the specimen collecting position of FIG. 7 to the transfer position of FIG. 9.

This engagement of the ramp on the first platform 72a with the roller 96 cams the platform 72a laterally, i.e., sideways to the left in FIG. 9, and thereby slides that platform 72a, on the slide rods 92 and against the restoring force of the spring 94, relative to the other second carriage platform 72b.

Figure 10:
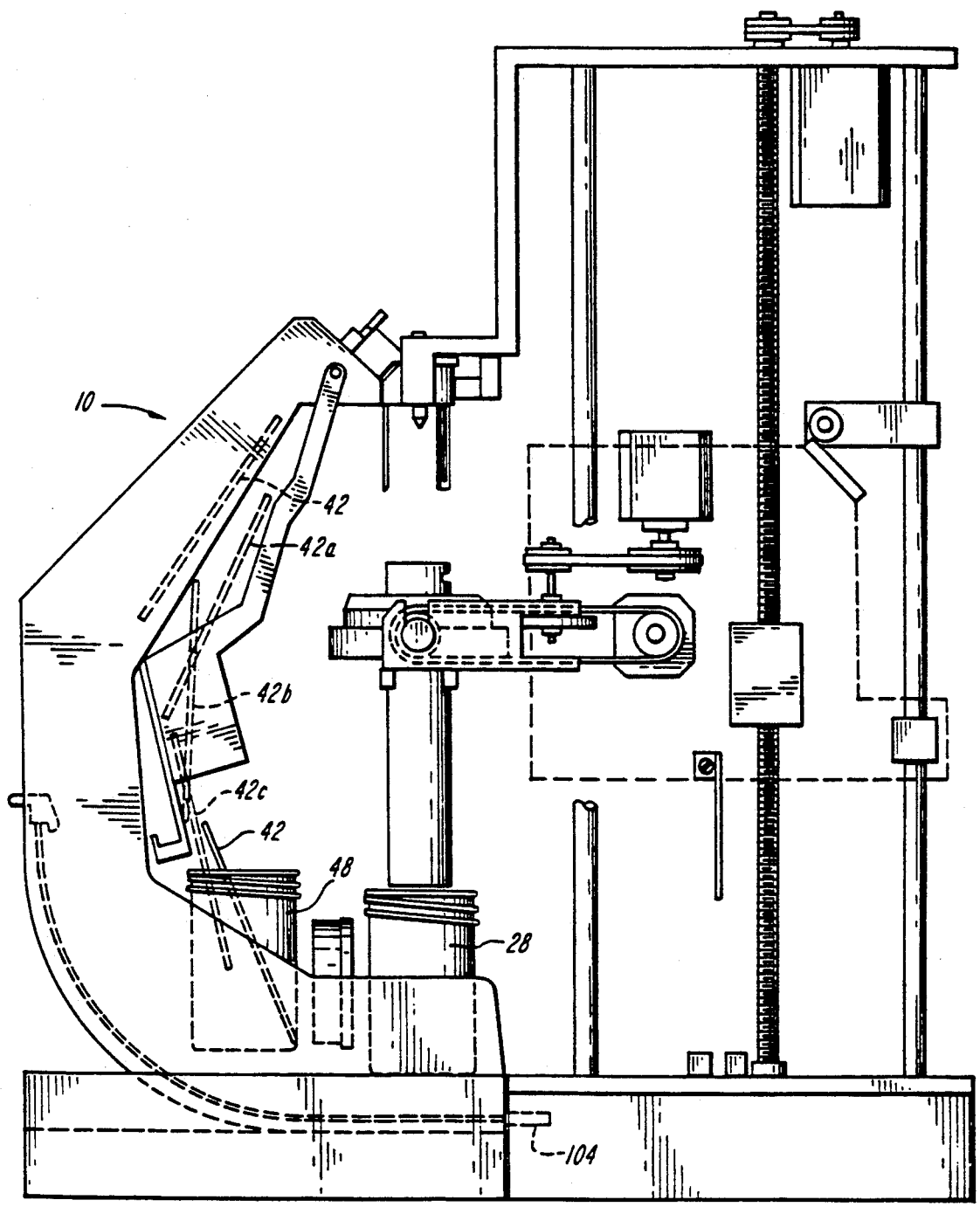

Further operation of the illustrated specimen processor 64, after completion of the specimen transfer to the microscope slide, is to retract the carriage platform 72a horizontally to the right and to return the jaw mechanism 86 of the manipulator 66 to the normal upright position. The specimen processor 64 performs these movements by lowering the carriage with the elevator motor 84 and by revolving the manipulator with the tilt motor 76a, to return the clamped filter device 36 to the upright position and centered on the vertical axis 30, as shown in FIG. 10. Thereafter, with the filter device 36 again centered on the axis 30 above the sample container 28, the specimen processor 64 can empty sample-suspending liquid, that was aspirated into the filter device 36 during the specimen collecting operation (FIG. 7), by closing the clamp 90 and applying a positive pressure to the filter device 36. This action expells the liquid through the screen filter 46 and, empties it back into the sample container 28.

Thereafter, the specimen processor 64 raises the carriage 72 and thereby raises the clamped filter device 36 to the position shown in FIG. 5. This movement returns the filter device to be seated in the socket-like receptacle 32 of the implement support 14 on the cartridge. With the clamp 90 open, the specimen processor 64 releases the jaw mechanism 86 of the manipulator 66 from clamped engagement with the filter device. The specimen processor next lowers the carriage 72 to the initial position of FIG. 4, where the manipulator 66 is entirely removed from the filter device 36.

A further operation, in the illustrated sequence, of the cartridge 10 of the invention with the specimen processor 64, is to transfer the microscope slide 42, with the cellular sample thereon, from the implement support 16 to a bath of fixative solution contained in an output container 48 seated in the output support 18. The processor 64 preferably performs this operation promptly after transferring a specimen to the slide 42 and hence prior to expelling liquid from the filter device and prior to returning the filter device to the cartridge support 14. The transfer mechanism 54 of the cartridge 10 performs this slide-transferring operation, in response to the processor, by disengaging the slide from the support 16 and by guiding the released slide 42 to enter the output container 28.

More particularly, the illustrated processor 64 has a solenoid actuator 104 (FIG. 4) that, when actuated, depresses a spring-biased plunger 106 (FIG. 11) mounted in the cartridge base 22. As also shown in FIG. 11, a flexible cable 108, guided in a passage 110 in the cartridge frame, couples the plunger 106 movement to operate the transfer mechanism 54. The further structure and operation of the transfer mechanism is set forth below.

The cartridge 10 typically is now removed from the engagement with the specimen processor 64, thereby readying the processor for repeating the foregoing operation with a fresh cartridge 10 carrying a fresh sample and fresh slide and fresh output container and fresh filter device 36.

Figure 11:
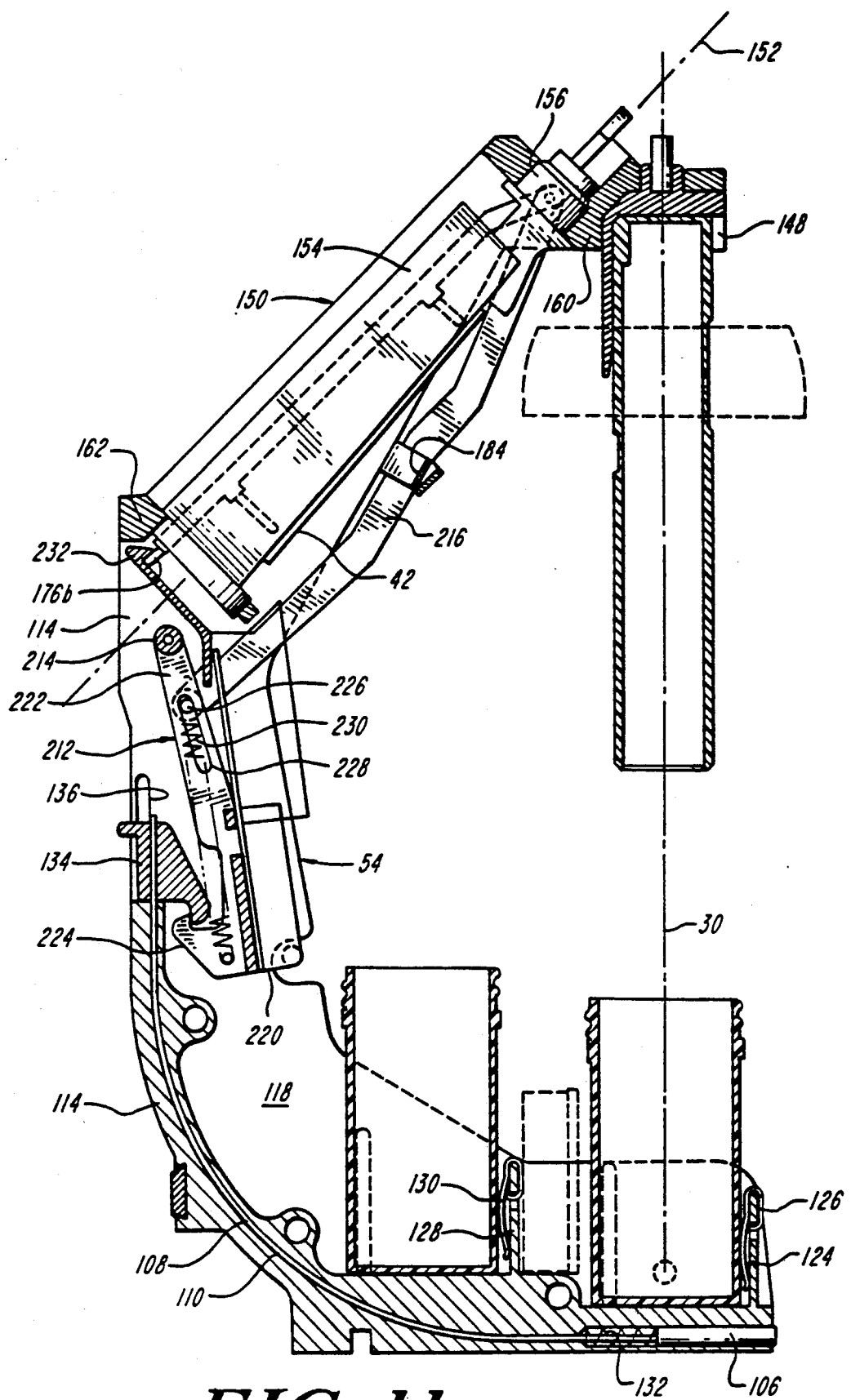
FIGS. 11 and 12 are side elevation views, partly broken away, of the cartridge of FIGS. 1 and 2 and showing the transfer mechanism respectively in a retracted position and in a slide-transferring extended position.

With reference to FIG. 2 and 11, the illustrated cartridge 10 has, as appears in the side profile view of FIG. 2, an upright and generally semi-circular shape. In the front view of FIG. 11, the cartridge has an overall upright columnar shape. The four supports are spaced around the semi-circular shape shown in FIG. 11, with the sample container support 12 lowermost at the six o'clock position, the output container support 18 at essentially the same level at approximately the seven o'clock position, the viewing screen support 16 located generally in the ten and eleven o'clock positions, and the filter device support 14 essentially uppermost at the noon position. Elements of the illustrated transfer mechanism 54 span roughly between the output location of support 18 and the support 14, across the support 16.

The cartridge frame 20 has an overall c-channel cross section with the opening facing into the center of the semi-circular side profile. The web 114 of this channel structure forms the base 22 of the frame 20 and the flanges 116 and 118 form side walls of the supports 12 and 18.

Aside from the reference pin 56 at the top of the cartridge 10, other reference aligning and positioning structure are generally lowermost on the frame 20. In particular, the pins 58 and 60 project from the flanges 116 and 118 respectively adjacent the cartridge base, as shown in FIGS. 2 and 11. Further, the frame base 22 is recessed along the bottom with two slide tracks 120, parallel and normally horizontally extending, and with a transverse track 122. These tracks are used for guiding the cartridge 10 into installation with a processor 64, for holding it in engagement with the processor, and otherwise engage with a conveyor or other mechanism for the automated machine transfer and movement of cartridges relative to a processor.

Figure 13:
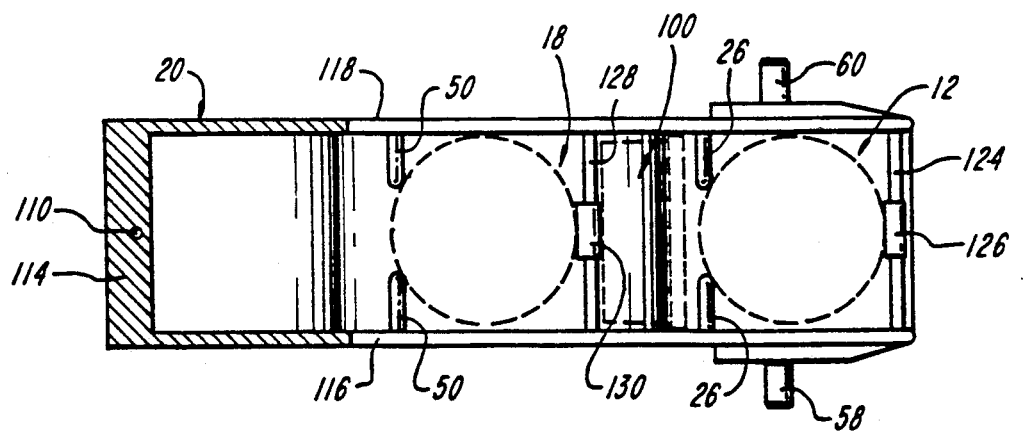
FIG. 13 is a view along line 13—13 of FIG. 1 showing the sample support and the output support of the cartridge of FIG. 1.

As shown in FIGS. 11 and 13, the socket-like receptacle of the support 12 is formed by a frame front wall 124 spanning between the flanges 116 and 118 and by two guides 26 projecting from the flanges into the channel structure. The frame base 20 forms the bottom of the support. The wall 124 preferably carries a leaf spring 126 resiliently projecting into the socket-like receptacle for biasing a sample container 28 seated therein against the guides 26.

Similarly, an internal wall 128 carrying a leaf spring 130 spans between the channel flanges 116 and 118 for forming the socket-like receptacle of the output container support 18, together with two opposed guides 50, projecting inwardly respectively from the flanges 116 and 118. The illustrated cartridge 10 further has a receptacle 100 on the frame 20 between the socket-like receptacles of the supports 12 and 28, that removably and replaceably receives and holds the cap 28a of the sample container 28.

The passage 110 that slideably receives and guides the cable 108 and the plunger 106, extends within the frame base 22 and channel web 114, as FIG. 11 shows. A spring 132 is seated within the passage 110 and compressed therein against the inner end of the plunger 106 to urge the plunger to the right in FIG. 11, to the normal position shown. The plunger is fixed to one end of the cable 108. The other end of the cable is fastened to the base of a latch 134 that is part of the transfer mechanism 54.

The base of the latch 134 is disposed in a cut-out in the channel web 114 and is seated in slots 136 that recess the web at the sides of the cut-out. The latch is slideable vertically along the slots to a lowermost normal position shown in FIG. 11, where the latch base abuts the frame web under the resilient bias of the spring 132. Depressing the plunger 106, i.e., moving it to the left in FIG. 11, which additionally compresses the spring 132, slides the cable 108 in the channel 110 and pushes the latch upward from the normal latching position of FIG. 11 to a release position discussed further below with reference to FIG. 12.

Figure 14:
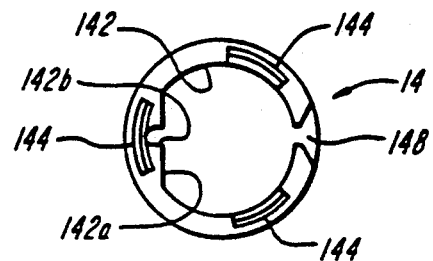
FIG. 14 is a fragmentary view along line 14—14 of FIG. 1 showing the first implement support of the cartridge of FIG. 1.

With reference to FIGS. 2 and 14, the filter device support 14 at the top of the frame 20 has an uppermost inner seat 142 from which three outer seat prongs 144 extend, parallel to the axis 30. The prongs 144 are equally spaced circumferentially to engage and receive telescopically a filter device 36 (FIG. 3). At least one prong 144 preferably carries a leaf spring 146 to enhance the resilient holding engagement of the outer seat prongs with a filter device. The outer seat formed by the three prongs 144 allows at least partial rotation, about the axis 30, of a filter device 36 seated therein.

The inner seat 142 of the support 14 is keyed and telescopically receives a filter device 36 only with one selected rotational orientation. The illustrated keyed structure is a flat surface 142a, recessed with a radially extending slot 142b and extending along a geometrical cord of the otherwise circular cross-section of the seat, as appears in FIG. 14.

The seat 142 is keyed in this manner to receive the tab 44a of the illustrated filter device 36 of FIG. 3 and, hence, to seatingly receive the filter device with only a selected rotational orientation, i.e., about the axis 30. This selected rotational orientation imposes a selected rotational orientation on the passage 44b and on the clamping surfaces 44c of the filter device seated at the support 14.

With further reference to the support 14, FIGS. 2 and 14 show a sensor aperture 148 that extends through the side wall of the support inner seat 142 at the front of the cartridge, which is the side facing to the right in FIG. 1. The sensing aperture 148 thus faces the specimen processor 64 (FIG. 4) for receiving a sensing device on the processor. That sensor device signals to the processor whether a cartridge 10 installed with the processor has a filter device seated fully in the support 14.

Figure 15:
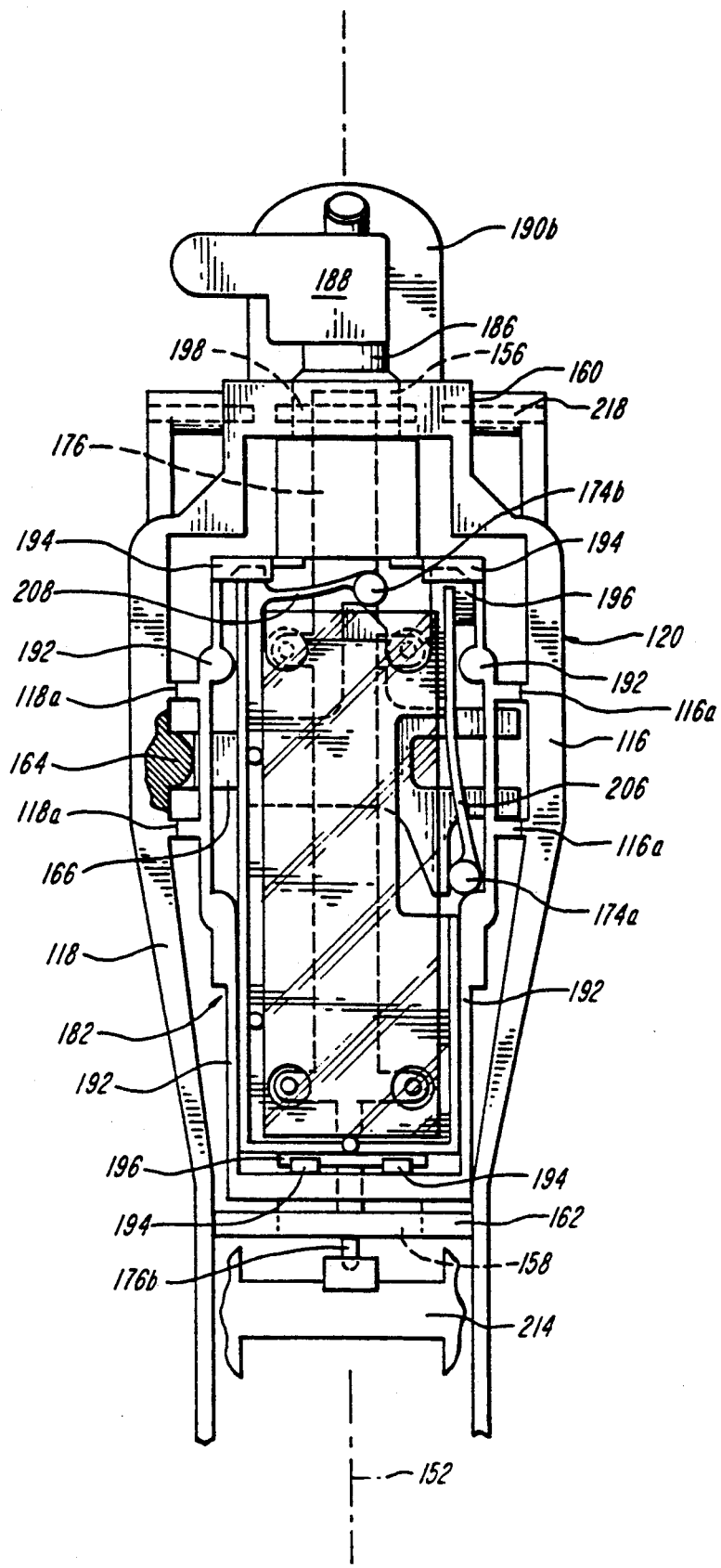
FIG. 15 is a fragmentary view of the cartridge of FIG. 1 along line 15—15 and showing a plan view of a cradle assembly according to the invention.
Figure 16A:
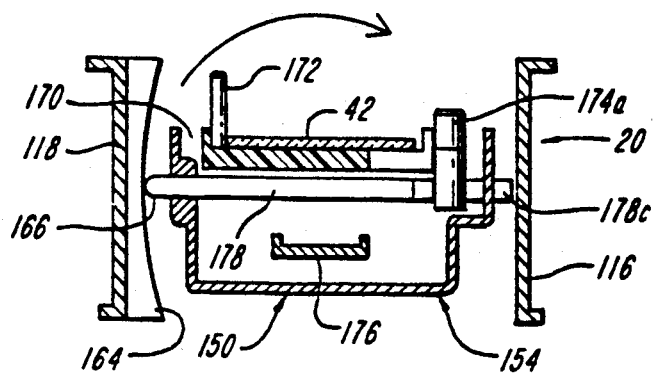
FIGS. 16A, 16B and 16C are simplified views of the cradle assembly of the cartridge of FIG. 1 in different rotational positions between a load position and a transfer position.
Figure 16B:
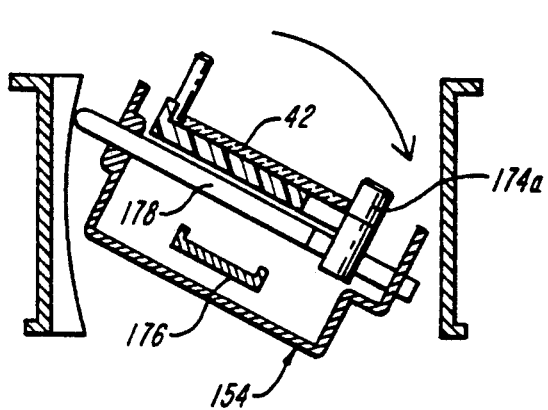
Figure 16C:
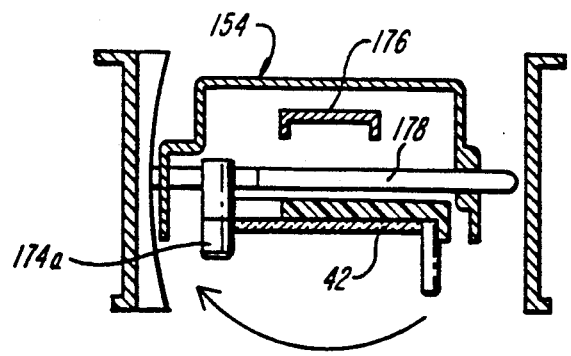

The second implement support 16 of the cartridge 10, for holding the microscope slide 42, has a cradle assembly 150 mounted to the cartridge frame 24 rotation about an axis 152 between a load position shown in FIGS. 15 and 16A and a specimen receiving position shown in FIGS. 11 and 16C. The cradle assembly is cammed open, to receive a microscope slide 42, when in the load position and is closed to clamp the microscope slide to it when in the specimen receiving position.

With reference to FIGS. 11 and 15, the cradle assembly has a cradle frame 154 that has short shafts 156 and 158 axially spaced apart along the axis 152. The shafts rotatably seat in journals formed by walls 160 and 162 of the cartridge frame 20, thereby mounting the cradle assembly 150 to the cartridge frame.

A cam 164, shown in FIG. 15, extends circumferentially on the inner wall of the frame flange 118 for slideable engagement with a follower 166 on the cradle frame 150 to open the clamping mechanism on the cradle assembly when the assembly is rotated to the load position of FIG. 15. The clamping mechanism is resiliently biased to the closed position, for holding a microscope slide 42 therein, when not cammed open by engagement with the cam 164.

Other major parts of the illustrated cradle assembly 150 include a slide holder 170, FIGS. 15, 16 and 17, having fixed pins 172 and movable pins 174a and 174b for holding engagement with the microscope slide 42. The cradle frame 154 carries the slide holder 170 to be openly exposed, as appears in FIG. 15, to receive a microscope slide when the frame is rotated to the load position. The slide holder 170 faces, on a diagonal parallel to axis 152, toward the specimen processor 64 and correspondingly toward a filter device 64 when the cradle frame is rotated t the specimen receiving position.

The cradle frame 154 also carries an ejector arm 176, FIGS. 15 and 18, that is part of the transfer mechanism 54; and has a camming plate 178, FIGS. 15 and 17, that cams the pins 174a and 174b of the slide holder 170 open for loading a microscope slide. A leaf spring 180, FIG. 18, of the cradle assembly 150 is secured between the slide holder 170 and the ejector arm 176. As shown and described further below, the illustrated cradle frame 154 has an open-fronted box structure carried on the end shafts 156 and 158 and which houses the slide holder 170, the camming plate 178 and the spring 180, and through which the ejector arm 176 extends.

More particularly, with reference to FIG. 15, the illustrated cartridge frame 20 has an open loading window 182 in the web along the length of the cradle frame 154. The journalled walls 160 and 162 join between the frame flanges 116 and 118 at upper and lower ends of this window, spaced apart along the axis 152. Further, as shown in FIG. 11, a bowed rib 184 spans between the frame flanges, opposite the window 182, for structural rigidity.

In addition to the cam 164 on the inner wall of the frame flange 118, both illustrated frame flanges 116 and 118 carry, on their opposed inner surfaces, a pair of guide bosses 116a and 118a respectively for slidable engagement with arcuate slide surfaces on the cradle frame 154.

With further reference to FIG. 15, the cradle frame 154 has a neck 186 extending along the axis 152, beyond the upper shaft 156, and from which a lever 188 projects. Manual rotation of the lever between the load position of FIGS. 15 and 16A and the specimen receiving position of FIGS. 3 and 16C rotate the cradle assembly 150 between these two positions. Stops 190a and 190b on the frame 20, shown in FIG. 3, limit the rotation of the lever 188 at these two positions.

The front of the cradle frame 154, which faces diagonally upward when in the load position of FIG. 15 and faces diagonally downward in the specimen receiving position of FIG. 3, seats the tray-like slide holder 170 within peripheral side and end wall portions 192 on the cradle frame, and shown in FIG. 15. Upper and lower end projections 194, on the front of the cradle frame 154, overlap projecting tabs 196 on the slide holder 170 to limit the movement of the slide holder 170 beyond the front of the cradle frame 154.

The back portion of the cradle frame 154, on the side opposite the front, accommodates the ejector arm 176 and mounts the leaf spring 180 on spring tabs located on the either side of the ejector arm, as shown in FIGS. 18A, 18C and 18D. The ejector arm 176 extends axially, relative to the diagonal axis 152, along essentially the entire length of the cradle frame 154 from a hinged mount 176a, at the upper end, that is hingedly pinned to the cradle frame 154 by a shaft 198 through the cradle frame upper shaft 156 (FIG. 15). As appears in FIGS. 15 and 18A, the major axial span of the ejector arm 176 extends along the back of the cradle frame 154 to a latch shelf 176b that extends beyond the lower cradle shaft 158 to project beyond the cradle frame 154.

The cradle frame 154 has a diametric slot 204 through the lower frame shaft 158 and through which the end of the ejector arm 176 adjacent the actuating shelf 176b projects. The ejector arm 176 thus moves with the cradle assembly about the axis 152 and, further, is rotatable about the shaft 198 at the upper hinge connection between a retracted position shown in FIGS. 18A and 18B and an eject position shown in FIG. 18C. The slot 204 through the frame shaft extends parallel to this latter hinged movement of the ejector arm lower end, and provides a slide guide for the movement of the ejector arm between the two positions of FIGS. 18A and 18C, respectively.

As shown in FIG. 15 and in FIGS. 18A, B and C, the ejector arm 176 carries a pair of laterally spaced ejector stems 176c. The ejector stems extend transversely to axis 152 and, accordingly, are directed from the back of the cradle frame toward the front, as shown in FIG. 18A. When the ejector arm 176 is in the retracted position of FIGS. 18A and 18B, the ejector stems 176c are spaced behind or in back of, the slide holder 170. However, as shown in FIG. 18C, when the ejector arm is moved to the eject position, the ejector stems project through openings 170a through the tray-like base of the slide holder 170. (As shown in phantom in FIGS. 17, 18A, B and C, an alternative is to provide additional ejector stems 176c on the arm and that project through additional openings 170a in the base of the slide holder; the four stems of the illustrated modification are spaced to underlie the four corners of a slide 42 on the holder 170.) A spring 210, FIGS. 18A, B and C, is seated in the cradle assembly 150 between the ejector arm 176 and the front of the cradle frame 154, and resiliently biases the arm to the retracted position of FIGS. 18A and B.

The leaf spring 180 secured to the back of the cradle frame 154, as illustrated in the detail of FIG. 18D has an overall side-view J-shape with the end of the handle portion being secured to the back wall of the cradle frame 154 and with the front of the crook portion disposed to underlie the tray portion of the slide holder 170. The illustrated spring 180 has two side-by-side portions, and the ejector arm 176 is disposed between them. A pressure tab of the spring 180 resiliently abuts the slide holder, as appears in FIGS. 18A through 18C. With this resilient mounting of the slide holder 170 within the cradle frame 154 and biased from the back wall of the cradle frame 154 by way of the leaf spring 180, the slide holder is normally resiliently disposed adjacent the front of the cradle frame, as FIG. 18A shows. However, upon abutting engagement by a filter device 36, as indicated in FIG. 18B, the slide holder is free to move, preferably with a rocking motion relative to the screen filter 46 on the filter device 36. This mounting of the slide holder 170 ensures intimate contact with the screen filter on a filter device for reliable and efficient transfer of cellular particles from the screen filter to the microscope slide 42 carried on the slide holder.

With reference to FIG. 15 and FIGS. 16A, B and C, the illustrated slide holder 170 has a generally tray-like structure with a tray surface 170b, for receiving thereon a microscope slide 42, and with a peripheral rim 170c. The holder 170 nests within the cradle frame 154, with the peripheral rim 170c slideably seating within the peripheral wall portions 192 of the cradle frame along lateral side portions of the slide holder 170. The end tabs 196 axially extend outwardly from the slide holder 170 at the upper and lower ends and slideably engage wall portions of the cradle frame 154 and further abut the frame projections 194 when the slide holder 170 is displaced fully to the front of the cradle frame 154. As also shown in FIG. 15, the tray surface 170b is apertured with the openings 170a through which the eject stems 176c of the ejector arm can extend, as shown in FIG. 18C. As noted above, the leaf spring 180 is compressed between the back of the cradle frame 154 and the underside of the slide holder tray surface 170b, as shown in FIGS. 18a through 18c.

With reference to FIG. 17 and to FIGS. 16A, B and C, the slide holding pins 172 are fixed inside the peripheral rim at the lower edge and at the one lateral side of the slide holder 170 that is adjacent the cam follower 166 on the camming plate 178. (This lateral side of the slide holder 170 appears on the left in FIG. 15).

The two moveable slide holder pins 174a and 174b, respectively located at the upper edge of the slide holder substantially opposite the lower edge pin 172 and adjacent the other lateral side of the slide holder, are each mounted on a spring arm 206 and 208, respectively. The other end of each spring arm 206, 208 is connected to the slide holder 170. The spring arm 206, which extends along a lateral side of the slide holder 170, resiliently biases the pin 174a that it carries inwardly, toward the opposed lateral side of the slide holder 170. Similarly, the spring arm 208, which extends along the upper end of the slide holder, resiliently urges the holder pin 174b which it carries inwardly relative to the slide holder tray surface and toward the lower rim.

The illustrated preferred slide holder 170 is molded of synthetic polymer to form the tray surface 170b and the peripheral rim 170c and the spring arms 206 and 208 and the moveable holder pins 174a and 174b as a single unitary structure, as appears in FIG. 17.

The fixed pins 172 and the moveable pins 174a and 174b all project upward from the slide holder tray surface 170b above the rim 170c, as appears in FIG. 16A. The two moveable pins 174a and 174b also project below the otherwise substantially flat surface of the slide holder 170, as FIG. 16A shows for the lateral moveable pin 174a. This downward extension of each moveable pin 174a and 174b abuttingly engages a deflecting surface 178a and 178b of the cam plate 178, as FIG. 17 shows.

The camming plate 178 is seated in the cradle frame 154 beneath the slide holder 170 and above the ejector arm 176 as shown in FIGS. 16A, B and C and FIG. 17. The cam plate 178 forms the cam follower 166 on a lateral extension on one side and has a lateral extension 178c on the opposite lateral side. These opposed lateral extensions extend through and slideably seat in slots in side walls of the box-structure of the carriage frame 154, as shown in FIGS. 15 and 16A, B and C. This slideable engagement, of the cam plate extensions with the side walls of the carriage frame, mounts the camming plate in the carriage assembly 150.

The camming plate is hence slideable laterally between a cammed position shown in FIG. 15 and a release position shown in FIG. 17. Shoulders on the camming plate, located adjacent the camming extension that forms the cam follower 166, abut the carriage frame to limit the movement of the camming plate in the release position. The spring arm 206 with the pin 174a at its end biases the cam plate 178 resiliently into the release position of FIG. 17. The laterally-acting deflecting surface 178a on the camming plate is laterally spaced from the moveable pin 174a of the slide holder, when the camming plate is moved to the release position, sufficiently to allow the pin 174a to clamp a microscope slide 42 as FIG. 17 shows. Movement of the camming plate to the cammed position, i.e., rightward in FIG. 17, abuts the deflecting surface 178a against the pin 174a and moves the pin rightward in FIG. 17, against the resilient bias of the spring arm 206.

With further reference to FIGS. 15 and 17, the axially-acting deflecting surface 178b on the camming plate extends diagonally relative to the peripheral sides and to the upper and lower ends of the slide holder tray. The surface 178b is closely spaced from the moveable pin 174b in the slide loading condition of FIG. 17. Movement of the camming plate from that release position toward the cammed position of FIG. 15, i.e., rightward movement in FIG. 17, brings the diagonal deflecting surface 178b into camming engagement with the moveable pin 174b and, accordingly, deflects the pin outward, i.e., upward in FIGS. 15 and 17, against the resilient bias of the spring arm 208. Accordingly, when the camming plate 178 is in the release position, i.e., shifted to the left as in FIG. 17, the moveable pins 174a and 174b of the slide holder move to clamping positions due to the action of the resilient spring arms 206 and 208, for clamping a microscope slide 42 onto the tray structure of the slide holder 170. Sliding movement of the camming plate from this release and slide-clamping position to the cammed position of FIG. 15, engages the deflecting surfaces 178a and 178b against the moveable pins 174a and 174b, respectively, and deflects the pins outward, out of engagement with a microscope slide 42. Accordingly, in this condition, a slide 42 can be loaded onto the slide holder.

FIG. 16A, which shows the cradle assembly 150 in the load position of FIG. 15, shows the cam follower 166 on the camming plate 178 engaged with the cam 164 on the flange 118 of the cartridge frame 20 for deflecting the cam plate 178 to the cammed position, i.e., to the right in FIG. 16A. In this position, the camming plate 178 shifts the moveable slide holder pins 174a and 174b outward, as in FIGS. 15 and 16A so that a microscope slide 42 can be freely placed on the slide holder 170.

Rotation of the cradle assembly 150 clockwise from the load position of FIG. 16A by a relatively small amount, typically in the order of 20° to 30°, slides the cam follower 166 along the cam 164 to camming positions of progressively lesser camming deflection. Accordingly, the camming plate 178, under the resilient bias of the spring arm 206, progressively shifts to the release position, i.e., shifts left from the cammed position of FIG. 16A. This action releases the moveable slide holder pins 174a and 174b which, accordingly, close under the action of the spring arms 206 and 208 into clamping abutment with a microscope slide 42 on the slide holder. Thus, this initial rotation of the carriage assembly, from the load position of FIG. 16A to the intermediate position of FIG. 16B, causes peripheral clamping of a microscope slide seated on the slide holder 170.

Figure 12:
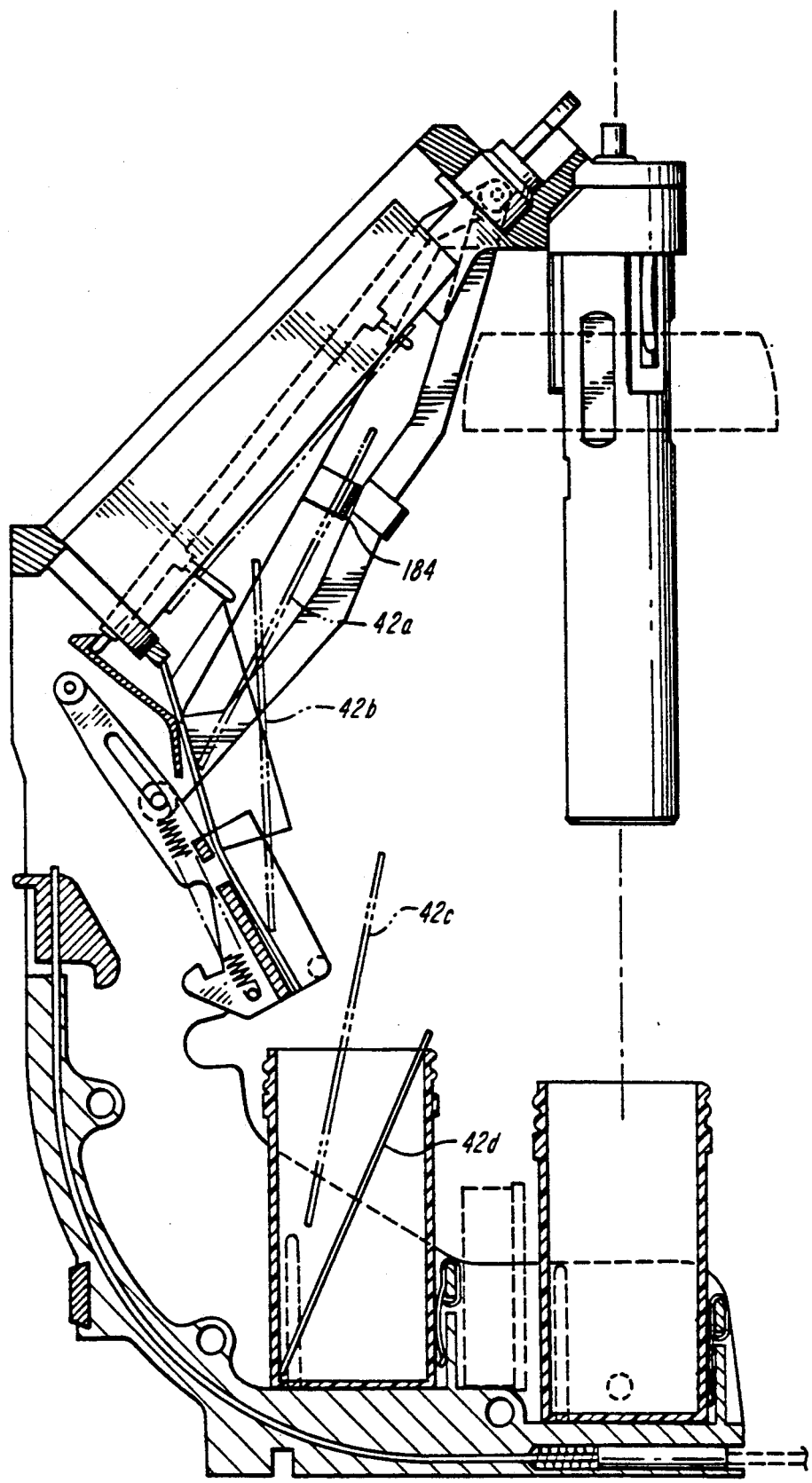

Upon further clockwise rotational movement of the carriage assembly 150, to the inverted specimen receiving position of FIG. 15C, the camming plate is free of engagement with the camming surface and can move fully to the release position. The slide 42 remains clamped to the slide holder. The several views of FIG. 18 and FIGS. 11 and 12, show the cartridge 10 with the carriage assembly 150 in the sample receiving position of FIG. 16C.

After the transfer of the biological specimen from the screen filter 46 of the filter device 36 to the microscope slide clamped in the carriage assembly 150, as discussed above with reference to FIG. 9 and indicated in FIG. 18B, the microscope slide 42 with the specimen thereon is transferred to a fixitive solution in the output container 48 seated in the output support 18, as previously discussed with reference to FIG. 10.

This slide transferring operation, which transfers the slide from the slide holder 170 of the carriage assembly to the output container, is illustrated in progressive stages in FIG. 12 and the transfer mechanism 54 for effecting this operation is described further below.

One element of the transfer mechanism 54 is the ejector arm 176 hinged at its upper end to the cradle frame 154 by the shaft 198 (FIG. 15) and extending longitudinal of the axis 152 along the length of the cradle frame 154 to an actuating tab 176b that projects beyond the lower end of the cradle frame 154.

Other elements of the transfer mechanism 154 are, as shown in FIGS. 2 and 11, the latch 134, a guide chute 212 hingedly mounted to the frame 20 by a shaft 214, and a swing bracket 216. The swing bracket has two side-by-side swing arms that are hingedly mounted to the frame 20 on aligned shafts 218 concentric with the ejector arm shaft 198. The bracket is linked at its lower end to the chute 212.

As shown in FIGS. 2, 11 and 12, the chute 212 is moveable about the hinged shaft 214 between a retracted position shown in FIG. 11 and a release position shown in FIG. 12. The chute has a walled slide 220 that it positions, when in the release position, to extend from the lower end of the carriage assembly 150 to directly above the output container 48 seated in the output support 18 of the cartridge. A pair of mounting arms 222 extends upward from the walled slide on the chute 212, in line with the slide, to the hinge connection formed with the shaft 214. That shaft extends between the frame flanges 116 and 118. The illustrated slide 220 has a lower section 220a integral with the arms 222 and has an upper section 220b hingedly joined to and extending upward from the lower section. The two slide sections are essentially aligned in the retracted position (FIG. 11) and are angled to form a curved slide structure in the release position (FIG. 12).

Behind the lower end of the walled slide 220, the chute 212 has a latch member 224 releasably engageable with the latch 134. When the guide chute 212 is retracted, FIG. 11, the latch member 224 is engaged with the latch 134 to prevent rotation of the guide chute 212 counterclockwise in FIG. 11 about the shaft 214. When the latch 134 is raised, by depressing the plunger 106, the latch member 224 is released and the guide chute 212 is free to rotate to the extended position of FIG. 12.

A slot 228 recesses each mounting arm 222. The mounting arms 222 slideably seat a slide rod 226 in the slots 228, and a spring 230 is tensioned between the rod 226 and a spring anchorage located on the chute 212 adjacent the lower end of the slide 220. The slide rod 226 is carried on the lower end of the swing arm 216.

As further shown in FIGS. 11 and 12, the swing bracket 216 carries, adjacent its lower end where the rod 226 is located, an upstanding finger 232 that latchingly engages the actuating tab 176b of the ejector arm 176.

The transfer mechanism 54 has a retracted position as shown in FIG. 11, where the guide chute 212 is rotated clockwise relative to the hinge shaft 214 to seat the latch member 224 in the frame-carried latch 134. Rotation of the guide chute 212 to this retracted position rotates the swing bracket 216 clockwise, about the hinge shafts 218, to dispose the rod 226 at the upper end of the arm slots 228, and thereby tensions the spring 230. The finger 232 on the swing bracket is also rotated into a clockwise position to ensure that it is latchingly engaged on the front side of the actuating tab 176b, as in FIG. 11. Note that the cradle assembly 150 can be rotated about the axis 152 between the load position of FIG. 16A and the specimen receiving position of FIG. 16C without interfering engagement with the transfer mechanism 54. This rotational movement of the cradle assembly 150 moves the ejector arm tab 176b between the position shown in FIGS. 11 and 18A and a position beyond the ejection position shown in FIG. 12.

When the transfer mechanism is in the retracted position of FIG. 11, and the frame latch 134 is raised to release the guide chute latch 224, the tensioned spring 230 draws the rod 226 downward in the arm slots 228. This action rotates the swing bracket 216 counterclockwise (FIG. 11) about its hinged connection with the frame. (Note that this is the same axis as the shaft 198, about which the ejector arm 176 rotates when the carriage assembly is in the specimen receiving position, as appears in FIG. 11 and 12.) The counterclockwise rotation of the swing bracket 216 rotates the guide chute 212 counterclockwise to the position shown in FIG. 12, due to the compound linkage between the swing bracket 216 and the guide chute 212, both of which are hinged to the cartridge frame 20. The movement stops when the slide rod 226 moves to the bottom of the arm slots 228. The counterclockwise rotation of the swing bracket 216 also moves the finger 232 through a counterclockwise ark and draws the actuating tab 176b on the ejector arm through the same movement. Accordingly, the ejector arm rotatingly moves counterclockwise from the position of FIG. 11 to the position of FIG. 12. As discussed above with reference to FIGS. 18A, B and C, this movement of the ejector arm moves the ejector stems 176c through the openings in the slide holder 170 and presses the microscope slide 42 out of engagement with the holder 170.

The microscope slide 42 accordingly is completely disengaged from the holder 170 momentarily, until it descends against the rib 184 (FIGS. 2 and 12) that spans between the frame flanges 116 and 118. This engagement of the slide with the frame rib 184 constrains the microscope slide to slide downward relative to the rib until the bottom edge of the slide engages the walled slide 220 of the guide chute 212. FIG. 12 shows the slide in this position with the numeral 42a. The descent of the microscope slide 42 continues, with the lower edge sliding along the walled slide 220, and reference number 42b designates the typical position of the slide in this descent after it has fallen free of the frame rib 184. The further descent of the microscope slide is guided by the walled slide 220, until the microscope slide falls free of the slide and into the output container as designated with the microscope slide in position 42c. The reference numeral 42d designates the final position of the microscope slide after it has come to rest within the output container 48.

The transfer mechanism is returned to the retracted position by manually moving the lower end of the walled slide 220 clockwise (FIG. 12) to engage the latch 224 with the frame carried latch 134. The mechanism accommodates this movement when the cradle assembly 150 is in any rotational position, i.e., between the positions shown in FIGS. 16A and 16C, and similarly the cradle assembly 150 can be rotated between these positions independently of the position of the transfer mechanism 54.

It will thus be seen that the objects set forth above, among those made apparent from the preceding description, are officially attained. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention described herein, and all statements of the scope of the invention which, as a matter of language, might be said to fall therebetween.

Having described the invention, what is claimed as new and secured by Letters Patent is:

1. Specimen holding and receiving apparatus for automated operation with specimen processing apparatus, said holding and receiving apparatus comprising
   A. frame means for removable and replaceable alignment and operative engagement with specimen processing apparatus and having reference surface means for removable and replaceable positional alignment with the specimen processing apparatus,
   B. first support means on said frame means for removably and replaceably supporting a container of a biological specimen having cellular particles suspended in liquid, said first support means normally supporting the container of biological specimen at a selected three-coordinate location relative to said reference surface means,
   C. second support means on said frame means for removably and replaceably supporting a specimen receiving implement adapted for receiving cellular particles from the container of the biological specimen, said second support means normally supporting said specimen receiving implement at a selected location relative to said reference surface means, and
   D. said frame means and said first and second support means being adapted for removable and replaceable alignment and engagement with the specimen processing apparatus for the removal, by the processing apparatus, of cellular particles from liquid suspension in a container of biological specimen said first support means to a specimen receiving implement at said second support means.

2. Specimen holding and receiving apparatus according to claim 1
   A. further comprising third support means on said frame means for removably and replaceably supporting an output container at a selected output location on said frame means,
   B. further comprising filter support means on said frame means for removably and replaceably supporting a screen filter device adapted for collecting cellular particles on a screen filter from suspension in liquid in a sample container at said first support means, and
   C. in which said several support means are disposed successively order along a first substantially planar and generally arcuate path.

3. Specimen holding and receiving apparatus according to claim 1 in which
   said specimen receiving implement includes an optical viewing screen adapted for receiving on a viewing surface thereof cellular particles collected from the liquid suspension.

4. Specimen holding and receiving apparatus according to claim 3
   A. in which said second support means includes engagement means having an open position and a closed position and adapted for receiving a viewing screen when in said open position and for holding a viewing screen in a selected three-coordinate location when in said closed position, and
   B. further comprising release means for removing a viewing screen from holding by said engagement means when said engagement means is in said closed position.

5. Specimen holding and receiving apparatus according to claim 3 further comprising
   A. further support means on said frame means for removably and replaceably supporting a further specimen receiving implement that includes screen filter means adapted for collecting cellular particles on a screen filter from suspension in liquid in a sample container at said first support means, said further support means normally supporting said further specimen receiving implement in a selected location, relative to said reference surface means, along three rectangular coordinates and about one rotational axis.

6. Specimen holding and receiving apparatus according to claim 3
   A. in which said second support means includes engagement means for receiving and holding the viewing screen in a selected three-coordinate location, and
   B. further comprising release means for removing the viewing screen from holding by said engagement means.

7. Specimen holding and receiving apparatus according to claim 6 further comprising
   A. third support means on said frame means for removably and replaceably supporting an output container at a selected output location on said frame means, and
   B. transfer means for transferring the viewing screen released from holding by said engagement means to an output container at said output location, said transfer means including guide means for guiding the gravitational descent of the viewing screen from said engagement means to entry into the output container.

8. Specimen holding and receiving apparatus according to claim 6 further comprising
   A. means forming output location means at a selected location on said frame means,
   B. transfer means for transferring to said output location a viewing screen released by said release means from holding by said engagement means, and
   C. means for linking said release means and said transfer means for substantially concurrent operation for removing the viewing screen from holding by said engagement means and for transferring the removed viewing screen to said output location in a substantially continuous operation.

9. Specimen holding and receiving apparatus according to claim 6 further comprising
   A. means forming output location means at a selected location on said frame means, and
   B. transfer means for transferring to said output location the viewing screen released by said release means from holding by said engagement means.

10. Specimen holding and receiving apparatus according to claim 9 in which
    said transfer means includes guide means for guiding the gravitational descent of a viewing screen from said engagement means to said output location.

11. Specimen holding and receiving apparatus according to claim 1
    in which said specimen receiving implement includes a screen filter device adapted for collecting cellular particles on a screen filter thereof.

12. Specimen holding and receiving apparatus according to claim 11
    in which said second support means includes means for removably and replaceably holding the screen filter device with selected location, relative to said reference surface means, along three rectangular coordinates and about one rotational axis.

13. Specimen holding nd receiving apparatus according to claim 11 further comprising further support means on said frame means for removably and replaceably supporting a further specimen receiving implement that includes an optical viewing screen adapted for receiving cellular particles collected on the screen filter device from liquid suspension in a container of biological specimen on said first support means.

14. Specimen holding and receiving apparatus according to claim 11
   A. in which said reference surface means includes a reference element centered on a first axis, and
   B. in which said first support means for the sample container and said second support means for the screen filter device are each centered on said first axis.

15. Specimen holding and receiving apparatus according to claim 14
   in which said second support means includes means for removably and replaceably holding the screen filter device with selected location, relative to said reference surface means along three rectangular coordinates and about said first axis.

16. Specimen holding and receiving apparatus according to claim 14
   A. further comprising further support means on the frame means for removably and replaceably supporting a further specimen receiving implement that includes an optical viewing screen adapted for receiving cellular particles collected on the screen filter device from liquid suspension in a container of biological specimen on said first support means,
   B. further comprising output support means on said frame means for removably and replaceably supporting an output container at a selected location on said frame means, and
   C. in which said further support means and said output support means are selectively aligned substantially along a first plane passing through said first axis.

17. Specimen holding and receiving apparatus according to claim 16
   in which said first support means, said second support means, said further support means, said output support means and said reference element are so structured that said first axis and said first plane are normally oriented vertically.

* * * * *